United States Patent
Umemoto et al.

(10) Patent No.: US 9,161,682 B2
(45) Date of Patent: Oct. 20, 2015

(54) MEDICAL SYSTEM AND CONTROL METHOD

(75) Inventors: Yoshitaka Umemoto, Hachioji (JP); Kazuhiko Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 71 days.

(21) Appl. No.: 13/154,878

(22) Filed: Jun. 7, 2011

(65) Prior Publication Data
US 2011/0295063 A1 Dec. 1, 2011

Related U.S. Application Data

(63) Continuation of application No. PCT/JP2010/071243, filed on Nov. 29, 2010.

(30) Foreign Application Priority Data

Mar. 2, 2010 (JP) .................................. 2010-045602

(51) Int. Cl.
| | | |
|---|---|---|
| *A61B 1/00* | (2006.01) | |
| *A61B 1/008* | (2006.01) | |
| *A61B 1/005* | (2006.01) | |
| *G02B 23/24* | (2006.01) | |

(52) U.S. Cl.
CPC ............... *A61B 1/008* (2013.01); *A61B 1/0016* (2013.01); *A61B 1/0057* (2013.01); *A61B 1/0052* (2013.01); *G02B 23/2476* (2013.01)

(58) Field of Classification Search
CPC .... A61B 1/005; A61B 1/0051; A61B 1/0052; A61B 1/0053; A61B 1/0055; A61B 1/0056; A61B 1/0057; A61B 1/0058; A61B 1/008; A61B 1/01

USPC ........... 600/104, 106, 114, 118, 139–152, 11; 604/523–528; 606/205–209
See application file for complete search history.

(56) References Cited

U.S. PATENT DOCUMENTS

| | | | |
|---|---|---|---|
| 7,348,751 | B2 | 3/2008 | Kawai et al. |
| 2002/0165430 | A1 | 11/2002 | Matsui |
| 2004/0138530 | A1 | 7/2004 | Kawai et al. |
| 2005/0168571 | A1* | 8/2005 | Lia et al. .......................... 348/82 |
| 2009/0253959 | A1* | 10/2009 | Yoshie et al. .................. 600/114 |

FOREIGN PATENT DOCUMENTS

| | | |
|---|---|---|
| CN | 101554335 A | 10/2009 |
| EP | 1 464 270 A1 | 10/2004 |
| JP | 06-022904 | 2/1994 |

(Continued)

*Primary Examiner* — Ryan Henderson
(74) *Attorney, Agent, or Firm* — Scully, Scott, Murphy & Presser, PC

(57) ABSTRACT

A medical system includes a movable portion configured to allow an angle to be changed within a predetermined angular range, an actuator configured to drive the movable portion so as to change the angle of the movable portion when a wire is pulled, a control unit configured to perform drive control of the actuator, a slack detection unit configured to detect a driving condition as to whether or not the wire is slack, a slack adjustment unit configured to adjust slack of the wire based on a detection result produced by the slack detection unit; and a slack adjustment command input unit used to input a command to adjust the slack of the wire, wherein the slack adjustment unit adjusts the slack of the wire to a predetermined state of adjustment in response to the command to adjust the slack of the wire.

23 Claims, 13 Drawing Sheets

(56) References Cited

FOREIGN PATENT DOCUMENTS

| JP | 2000-300511 | 10/2000 |
|----|-------------|---------|
| JP | 2002-323661 | 11/2002 |
| JP | 2004-041538 | 2/2004 |
| JP | 2007-054307 | 3/2007 |
| JP | 2007-283115 | 11/2007 |
| JP | 2007-319622 | 12/2007 |
| JP | 4436479 | 3/2010 |

* cited by examiner

MEDICAL SYSTEM AND CONTROL METHOD

CROSS REFERENCE TO RELATED APPLICATION

This application is a continuation application of PCT/JP2010/071243 filed on Nov. 29, 2010 and claims benefit of Japanese Application No. 2010-045602 filed in Japan on Mar. 2, 2010, the entire contents of which are incorporated herein by this reference.

BACKGROUND OF THE INVENTION

1. Field of the Invention

The present invention relates to a medical system equipped with a medical instrument which drives angles of movable portions such as a bending portion by pulling a wire as well as to a control method.

2. Description of the Related Art

Recently, various medical devices equipped with a bending portion configured to be bendable have been developed. For example, endoscopes and treatment instruments equipped with a bending portion on a distal end side of an insertion portion inserted into a body are widely used in a medical field.

Also, a lesion or the like in the body is treated using a treatment instrument passed into a treatment instrument channel provided in an endoscope. Sometimes treatments are administered with a treatment instrument under observation with an endoscope without using a treatment instrument channel.

Also, an active treatment instrument and the like equipped with driving means (actuator) configured to electrically drive the bending portion to improve operability have been put into actual use. Medical devices such as active treatment instruments provided with a bending portion on a distal end side have a configuration in which the bending portion and the driving means are connected with each other via an angle wire (hereinafter abbreviated to a wire) and the wire is driven by pulling by the driving means provided on a user's hand side to drive the bending portion on the distal end side.

With this configuration, the wire passed through a flexible, elongated member between the bending portion and the driving means on the user's hand side needs to be inserted into a body cavity in a flexed state, which makes it structurally difficult to completely avoid slack in the wire. Also, due to the slack, an amount of driving by the driving means on the user's hand side is not always equal to an amount of operation of the bending portion on the distal end side.

Thus, for example, a first conventional example, namely an endoscope disclosed in Japanese Patent Application Laid-Open Publication No. 2000-300511, is configured to remove slack from a wire by controlling the slack using tension information detected by a tension sensor adapted to detect tension acting on the wire.

Also, a second conventional example, namely a control apparatus disclosed in Japanese Patent Application Laid-Open Publication No. 2007-283115, is configured to remove any wire slack in order to improve responsiveness in driving to bend a bending portion in response to a user's operation command.

SUMMARY OF THE INVENTION

According to one aspect of the present invention, there is provided a medical system including: a movable portion installed in a medical instrument, made up of a plurality of pivotally coupled movable members, and configured to allow an angle to be changed within a predetermined angular range in at least one plane; an actuator installed in the medical instrument and configured to drive the movable portion so as to change the angle of the movable portion when a wire coupled to the movable portion is pulled; a control unit configured to perform drive control of the actuator; a slack detection unit configured to detect a driving condition as to whether or not the wire is slack; a slack adjustment unit configured to adjust slack of the wire based on a detection result produced by the slack detection unit as to whether or not the wire is slack; and a slack adjustment command input unit used to input a command to adjust the slack of the wire to the slack adjustment unit, wherein when the command to adjust the slack is inputted, the slack adjustment unit adjusts the slack in two mutually opposite directions such that there will be a predetermined relationship between an amount of slack of the wire in one of the two directions and an amount of slack of the wire in another direction based on the detection result detected by the slack detection unit regarding the slack of the wire in at least the two directions when the wire is pulled so as to reciprocate the angle of the movable portion in the two directions.

According to another aspect of the present invention, there is provided a control method for controlling operation of an actuator configured to drive a bending portion so as to change a bending angle of the bending portion via pulling operation of a wire, the control method comprising: a slack detection step of detecting a driving condition as to whether or not the wire is slack; a first slack adjustment step of adjusting slack of the wire based on a detection result produced by the slack detection step as to whether or not the wire is slack; a command input step of inputting a command to adjust the slack of the wire; and a second slack adjustment step of adjusting the slack of the wire to a predetermined state of adjustment with a known amount of slack based on the command to adjust the slack of the wire inputted by the command input step, based on a detection result detected by the slack detection step regarding the slack of the wire in two mutually opposite bending directions when the wire is pulled so as to reciprocate the bending angle of the bending portion in the two bending directions.

DETAILED DESCRIPTION OF THE PREFERRED EMBODIMENTS

Embodiments of the present invention will be described below with reference to the drawings.

First Embodiment

Figure 1:
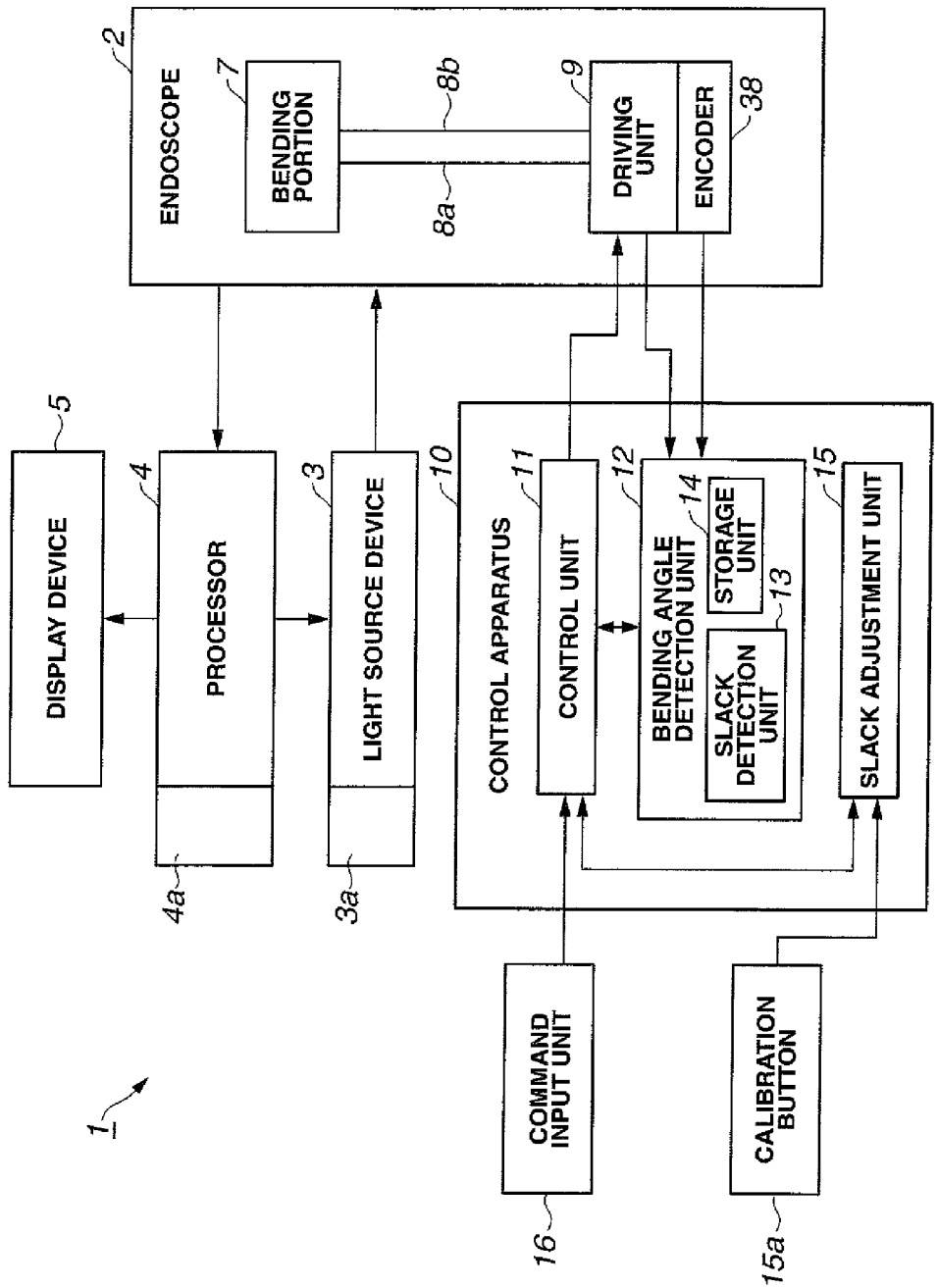
FIG. 1 is a block diagram showing an overall configuration of an endoscope system according to a first embodiment of the present invention.

As shown in FIG. 1, an endoscope system 1 according to a first embodiment of the present invention includes an endoscope 2 which is a medical instrument equipped with a built-in image pickup device, a light source device 3 configured to supply illuminating light to the endoscope 2, a processor 4 which is a signal processing unit configured to perform signal processing for the image pickup device, and a display device 5 configured to display an image picked up by the image pickup device 29 (see FIG. 2), as an endoscopic image when a video signal refined by the processor 4 is inputted.

Figure 2:
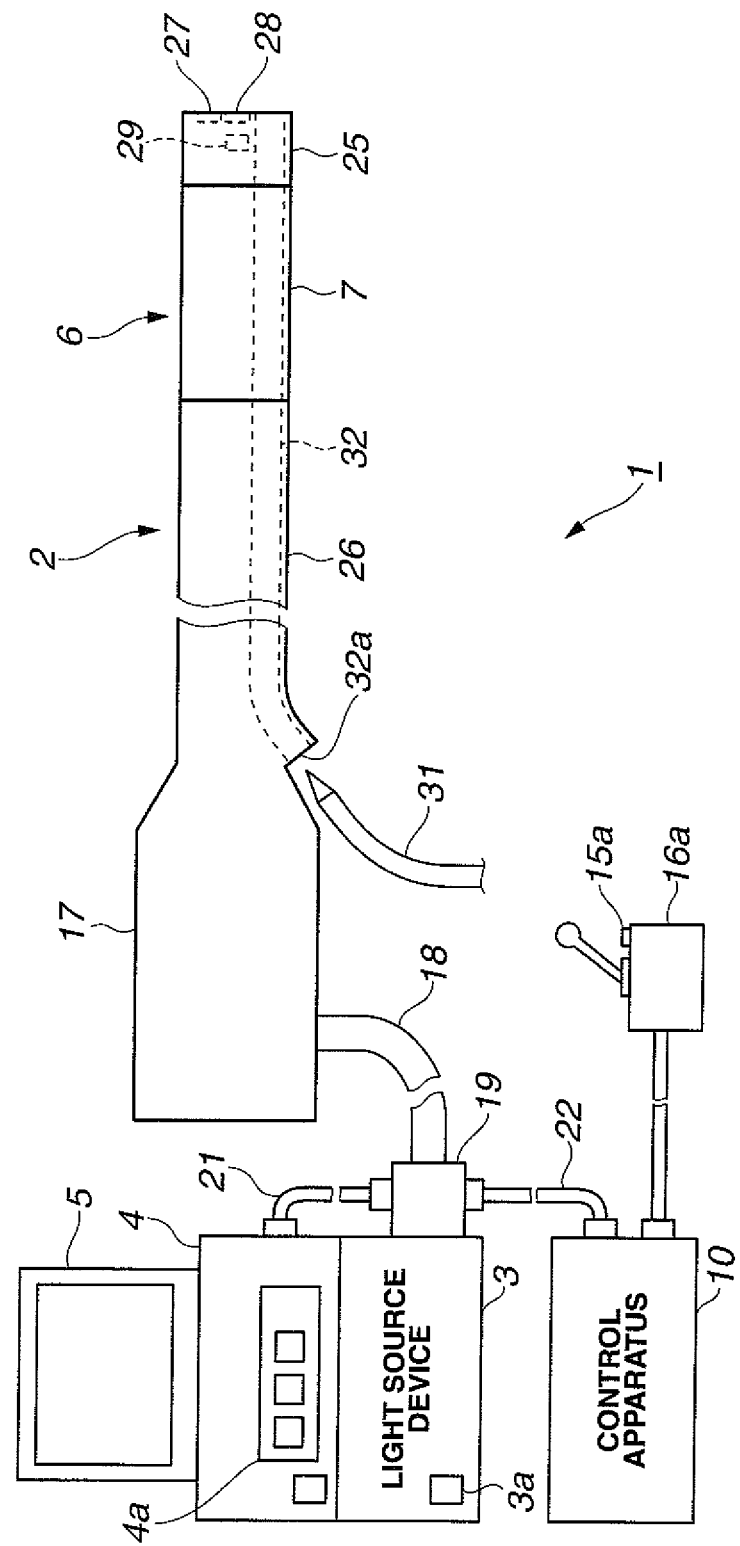
FIG. 2 is a diagram showing an external shape of an endoscope and the like shown in FIG. 1.

Also, the endoscope 2 is provided with a bending portion 7, which is a bendable, movable portion, on a distal end side of an insertion portion 6 (see FIG. 2). The bending portion 7 is connected via a pair of wires 8a and 8b to a driving unit 9 which makes up an actuator configured to remotely drive the bending portion 7.

Also, the endoscope system 1 includes a control unit 11 configured to control driving operation of the driving unit 9, a bending angle detection unit 12 configured to detect a bending angle of the bending portion 7, and a slack adjustment unit 15 configured to adjust (or calibrate) slack of the wires 8a and 8b via the control unit 11.

The bending angle detection unit 12 includes a slack detection unit 13 configured to detect (determine) a driving condition as to whether or not the wires 8a and 8b have slack based on a driving condition of the driving unit 9 and a storage unit 14 configured to prestore information about operating characteristics (of driving to bend) or operation parameters of the driving unit 9 and the bending portion 7 driven to bend.

Figure 3:
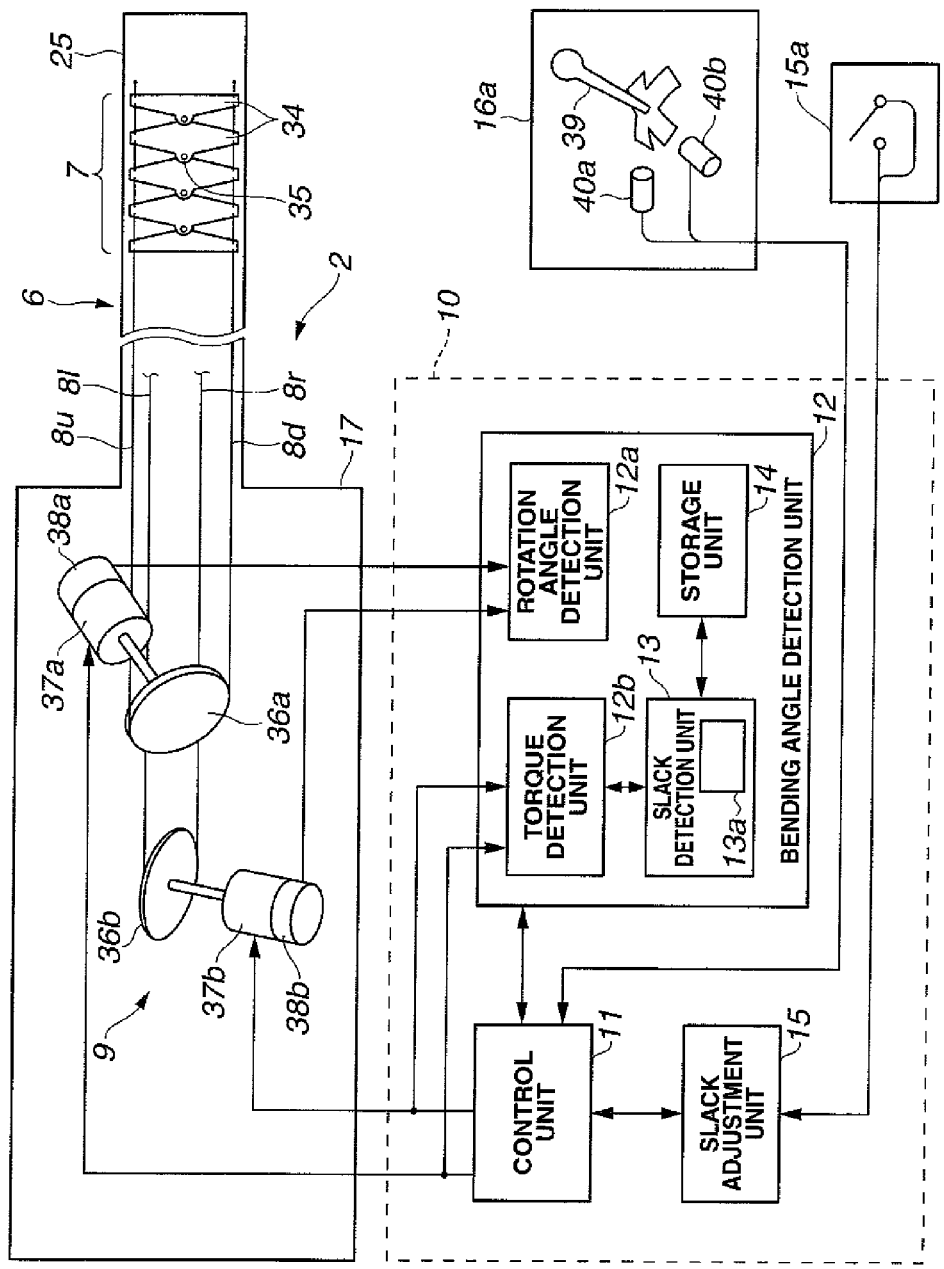
FIG. 3 is a diagram showing a configuration of the endoscope and a control unit.

The driving unit 9 is made up of motors 37a and 37b for rotational driving, as described later. Also, as shown in FIG. 3, the bending angle detection unit 12 configured to detect the bending angle of the bending portion 7 includes a rotation angle detection unit 12a and a torque detection unit 12b, where the rotation angle detection unit 12a is configured to detect rotation angles of the motors 37a and 37b of the driving unit 9 by serving as amount-of-driving detection means configured to detect an amount of driving of the driving unit 9 and the torque detection unit 12b is configured to detect torque of the motors 37a and 37b by serving as amount-of-driving-force detection means configured to detect an amount of driving force of the driving unit 9.

The rotation angle detection unit 12a detects the rotation angles of the motors 37a and 37b based on sensing signals as output signals of encoders 38 (collectively for 38a and 38b) configured to sense amounts of rotational displacement of the motors 37a and 37b while the torque detection unit 12b detects torque as amounts of driving force of rotation (moments of force) based on values of current of drive signals for driving the motors 37a and 37b.

By detecting a load on the driving unit which makes up the actuator or loads on the wires 8a and 8b, the slack detection unit 13 detects whether or not the wires 8a and 8b are in a driving condition with slack.

In the present embodiment, the slack detection unit 13 detects a driving condition as to whether or not the wires 8a and 8b are slack, by comparing torque values of the motors 37a and 37b detected by the torque detection unit 12b with a positive torque threshold Tth set in order to detect (determine) slack. That is, the slack detection unit 13 detects whether the absolute values of the detected torque values are equal to or higher than the threshold Tth meaning that there is no slack or the absolute values of the detected torque values are less than the threshold Tth meaning that there is slack.

Incidentally, values of current may be detected instead of torque values. Then, by comparing the detected values of current with a threshold set in order to detect (determine) slack, it may be detected whether the detected values of current are equal to or higher than the threshold meaning that there is no slack or the detected values of current are less than the threshold meaning that there is slack.

Also, a control apparatus 10 is connected with a command input unit 16 used by a user such as a surgeon to input a command to bend the bending portion 7 and a calibration button 15a made up of an ON/OFF switch and configured as a slack adjustment command input unit used to input a command to adjust the slack of the wires 8a and 8b to the slack adjustment unit 15.

When the calibration button 15a is manipulated by the user, the slack adjustment unit 15 operates to adjust slack of the wires 8a and 8b via the control unit 11 and causes the slack detection unit 13 to detect whether or not there is slack under the driving condition at that point and detect an amount of slack if there is any slack. If there is any slack, the slack adjustment unit 15 makes an adjustment to achieve a predetermined state of adjustment with a zero amount of slack or a known amount of slack based on a detection result produced by the slack detection unit 13.

Incidentally, although in FIGS. 1 and 2, the slack adjustment unit 15 is configured to use the detection result produced by the slack detection unit 13, via the control unit 11, the slack adjustment unit 15 may be configured to use the detection result produced by the slack detection unit 13, without involving the control unit 11.

The light source device 3 is provided with a light command switch 3a used to give a command to light a lamp in the light source device 3. The processor 4 is provided with a command input unit 4a used to give commands instructing the processor 4 to perform various types of signal processing. The user can give, for example, a white balance adjustment command via the command input unit 4a.

FIG. 2 shows appearance of the endoscope 2 and the like.

The endoscope 2 includes the insertion portion 6 inserted into a subject such as a patient, an operation portion 17 installed at a rear end of the insertion portion 6, and a universal cable unit 18 extended out from the operation portion 17.

A connector 19 installed at an end portion of the universal cable unit 18 is detachably connected to the light source device 3.

A first cable 21 extended out from the connector 19 is detachably connected to the processor 4. Also, a second cable 22 extended out from the connector 19 is detachably connected to the control apparatus 10.

The control apparatus 10 is connected with a joystick device 16a of the command input unit 16 used to input a command to bend the bending portion 7. The joystick device 16a is also provided with the calibration button 15a.

The insertion portion 6 of the endoscope 2 includes a distal end portion 25 installed at a distal end of the insertion portion 6, the bending portion 7 installed at a rear end of the distal end portion 25 and configured to be bendable, and a flexible portion 26 having flexibility and running from a rear end of the bending portion 7 to a front end of the operation portion 17.

An illumination window 27 and an observation window 28 are installed at the distal end portion 25 and an illumination lens (not shown) and a distal end portion of a light guide are placed inside the illumination window 27. The light guide is passed through the insertion portion 6, the operation portion 17, and the universal cable unit 18, with a rear end of the light guide reaching the connector 19.

When the connector 19 is connected to the light source device 3, illuminating light from the light source device 3 is incident on the rear end of the light guide, the light guide transmits the incident illuminating light, and the transmitted illuminating light is emitted through the illumination window 27.

An object illuminated by the illuminating light is focused by an objective lens installed in the observation window 28 on an image pickup surface of the image pickup device 29 such as a CCD placed at an image forming location.

The image pickup device 29 is connected to the processor 4 via a signal line (not shown). The processor 4 drives the image pickup device 29, performs signal processing on an image pickup signal subjected to photoelectric conversion by the image pickup device 29, generates a video signal, and outputs the video signal to the display device 5. The display device 5 displays images corresponding to the video signal, i.e., images picked up by the image pickup device 29, as endoscopic images.

A channel 32 is provided in the insertion portion 6 to allow passage of a treatment instrument 31 and an end portion of the channel 32 on the user's hand side opens as an insertion port 32a near the rear end of the insertion portion 6.

The surgeon can insert the treatment instrument 31 through the insertion port 32a, protrude a distal end side of the treatment instrument 31 from a distal opening of the channel 32, and thereby therapeutically treat an affected area and the like.

FIG. 3 shows a structure of the bending portion 7 as well as a configuration of the driving unit 9 and the like configured to drive to bend the bending portion 7 by pulling two pairs of wires 8u and 8d, and 8l and 8r.

As shown in FIG. 3, at the rear end of the distal end portion 25 of the insertion portion 6 cylindrical in shape, a plurality of substantially annular, bending pieces 34 (serving as a plurality of movable members) are pivotally coupled together by rivets 35 along a longitudinal direction of the insertion portion 6, forming the bending portion 7, where the rivets 35 serve as pivotal support members (for pivotal support).

A direction in which each bending piece 34 bends depends on installation locations of the rivets 35. According to the present embodiment, the rivets 35 are placed in up-and-down positions and left-and-right positions alternately. Thus, the bending pieces 34 are configured to be bendable in an up-and-down direction in a plane in the up-and-down direction orthogonal to the left-and-right positions by means of the rivets 35 placed in the left-and-right positions, and bendable in a left-and-right direction in a plane in the left-and-right direction orthogonal to the up-and-down positions by means of the rivets 35 placed in the up-and-down positions.

The bending portion 7 has a bending angle (initial angle) of almost 0 in an initial state in which the bending portion 7 is not driven to bend. Starting from the initial angle, the bending portion 7 can be bent in the up-and-down direction, i.e., two directions on both sides of the initial angle, as well as in the left-and-right direction, i.e., two directions orthogonal to the up-and-down direction. Although respective centers (angles) of predetermined bendable angular ranges in the up-and-down direction and the left-and-right direction are described below as being the initial angles in the initial state, this is not restrictive.

Incidentally, only the rivets 35 used for bending in the up-and-down direction are shown in FIG. 3 for the sake of simplicity. Two pairs of wires 8u and 8d and 8l and 8r for bending in the up-and-down direction and the left-and-right direction are passed through the insertion portion 6. Distal ends of the pairs of wires 8u and 8d and 8l and 8r are anchored to the most distal bending piece 34 or to the distal end portion 25 to which the most distal bending piece 34 is fixed.

Rear ends of the pairs of wires 8u and 8d and 8l and 8r are looped over a pulley 36a for up-and-down bending and a pulley 36b for left-and-right bending placed in an expanded diameter of the operation portion 17 at the rear end of the insertion portion 6.

Centers of rotation of the pulleys 36a and 36b are coupled to rotating shafts of the electric motors (hereinafter referred to simply as motors) 37a and 37b, respectively, and the motors 37a and 37b are rotated forward and backward freely by drive signals from the control unit 11.

Along with the rotations of the motors 37a and 37b, the respective pulleys 36a and 36b rotate, pulling and relaxing the respective wires 8u and 8d and 8l and 8r looped over the respective pulleys 36a and 36b. Consequently, the bending portion 7 is driven to bend in the direction of the pulled wires.

Also, in the present embodiment, encoders 38a and 38b are installed on the rotating shafts of the motors 37a and 37b. The encoders 38a and 38b sense the rotation angles of the motors 37a and 37b or pulleys 36a and 36b and output sensing signals.

The present embodiment is configured such that the bending angle of the bending portion 7 can be detected based on the rotation angles and the like of the motors 37a and 37b or pulleys 36a and 36b. The actuator which electrically drives to bend the bending portion 7 includes the motors 37a and 37b of the driving unit 9, the pulleys 36a and 36b, and the encoders 38a and 38b.

The drive signals for driving the motors 37a and 37b are inputted to the torque detection unit 12b configured to detect torque T as amounts of driving force of rotation (moments of force) of the motors 37a and 37b. The torque detection unit 12b detects the torque T based on electrical characteristics of the motors 37a and 37b and on the values of current of drive signals for driving to bend the bending portion 7 via the wires 8u, 8d, 8l, and 8r.

Incidentally, although FIG. 2 shows a configuration in which the endoscope 2 and the control apparatus 10 are interconnected via the cable 22, this configuration is not intended to be limiting. For example, the control apparatus 10 may be installed in the operation portion 17.

When the pulleys 36a and 36b are rotated, amounts of pulling of the wires 8u, 8d, 8l, and 8r are determined according to the rotation angles (amounts of rotation) of the pulleys 36a and 36b, and the bending portion 7 bends according to the amounts of pulling. Therefore, by detecting the rotation angles of the motors 37a and 37b or the pulleys 36a and 36b, basically the bending angle of the bending portion 7 can be detected.

In the present embodiment, the rotation angle detection unit 12a detects the rotation angles of the motors 37a and 37b or the pulleys 36a and 36b, based on, for example, the sensing signals from the encoders 38a and 38b mounted on the rotating shafts of the motors 37a and 37b. Also, the present embodiment is configured such that the bending angle of the bending portion 7 is estimated from the rotation angles of the motors 37a and 37b or the pulleys 36a and 36b.

However, since the wires 8u, 8d, 8l, and 8r (hereinafter 8u or 8l is represented by 8a while 8d or 8r is represented by 8b) can be in a driving condition in which there is slack, in the present embodiment, any such slack is detected and adjusted or corrected appropriately.

Also, for example, the joystick device 16a of the command input unit 16 includes a joystick 39 configured to be tiltable in any of the up-and-down and left-and-right directions and encoders 40a and 40b configured to detect tilt angles of the joystick 39 in the up-and-down direction and left-and-right direction, respectively.

The direction in which the joystick 39 is tilted corresponds to a specified bending direction of the bending portion 7 and the tilt angles correspond to specified values of the bending angle of the bending portion 7.

Sensing signals from the encoders 40a and 40b are inputted, for example, to the control unit 11. That is, the control unit 11 accepts inputs of the specified bending direction and the specified values of the bending angle from the joystick device 16a serving as bend command input means.

Based on the specified values, the control unit 11 determines the rotation angles of the motors 37a and 37b by referring to information stored in the storage unit 14 and rotationally drives the motors 37a and 37b such that the rotation angles of the motors 37a and 37b detected by the encoders 38a and 38b will follow the specified values.

Actually, since the wires 8a and 8b may be slack, according to the present embodiment, the torque detection unit 12b detects the torque T of the motors 37a and 37b. The slack detection unit 13 compares the torque T of the motors 37a and 37b with the positive torque threshold Tth set in order to detect whether or not there is slack and determines (detects) whether or not there is slack (under the current driving condition or operating condition) based on a result of the comparison.

If the slack detection unit 13 produces a detection result indicating that there is slack, the control unit 11 adjusts the motors 37a and 37b so as to remove the slack of the wires 8a and 8b (under the current driving condition).

Also, when the slack detection unit 13 produces a detection result indicating that there is slack, since operation under this condition is different from operation under normal driving condition in which there is no slack (e.g., the bending portion 7 does not rotates even if the motor 37a rotates), the slack detection unit 13 corrects the rotation angles of the motors 37a and 37b via the control unit 11.

That is, the slack detection unit 13 functions as a correction unit 13a configured to correct the rotation angles (of the motors 37a and 37b corresponding to the bending angle of the bending portion 7) under the current driving condition.

Also, the correction unit 13a performs control so as to store information about the driving condition (torque and rotation angles) of the motors 37a and 37b and the bending angle of the bending portion 7 together with (information about) time in the storage unit 14 in time sequence. In this way, by storing driving conditions (also referred to as operating conditions) in time sequence, it is possible to accurately manage the driving conditions of the motors 37a and 37b as well as states of the bending angle of the bending portion 7 by associating them with each other at each moment, allowing the bending portion 7 to be driven to bend accurately.

Incidentally, block configurations shown in FIGS. 1, 3, and the like are merely a configuration example of functional blocks, and are not intended to be limiting. For example, the control unit 11 may be configured to include functions of the bending angle detection unit 12, the storage unit 14, and the slack adjustment unit 15.

Figure 8:
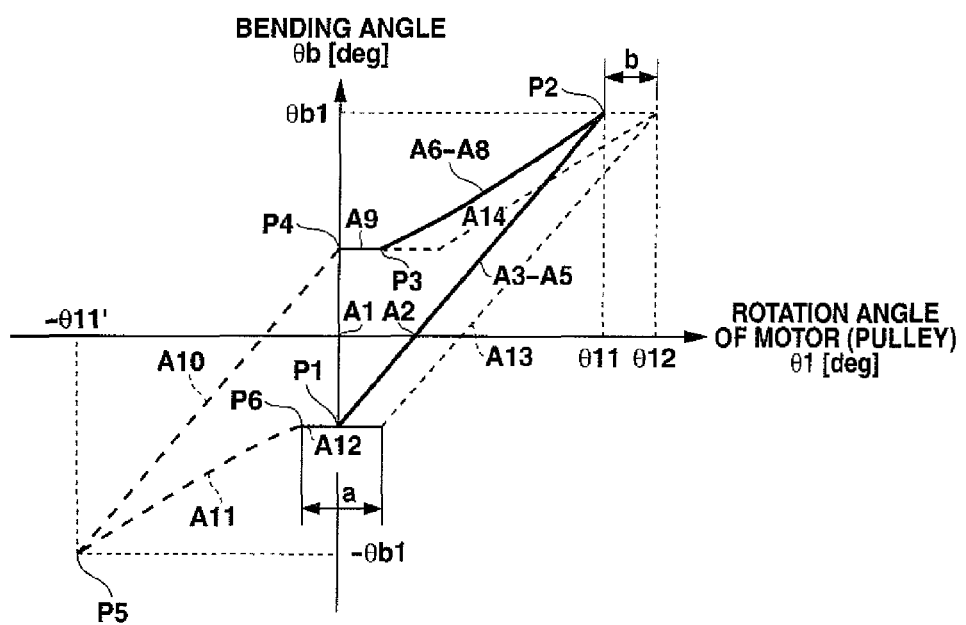
FIG. 8 is an explanatory diagram showing a rotation angle and the bending angle corresponding to FIG. 7.

As described above, the storage unit 14 prestores information (data) on operating characteristics which associates the rotation angle $\theta 1$ of the motors (pulleys) such as shown in FIG. 8 described later and the bending angle $\theta b$ of the bending portion 7 with each other within a bendable range of the bending portion 7. The information on operating characteristics stored in the storage unit 14 has hysteresis characteristics.

The information (data) is defined by coordinate positions represented by P1 to P2 (A5), P2 to P3 (A6-A8), P4 to P5 (A10), and P5 to P6 (A11) in an example shown in FIG. 8 (where the abscissa represents the rotation angle $\theta 1$ and the ordinate represents the bending angle $\theta b$) and is approximated by a rhombus. The data differs from those parts of operating characteristics which are affected by slack and vary with the operating environment, such as the parts indicated by A1-A2, A9, and A12.

The storage unit 14 may store the information about operating characteristics such as shown in FIG. 8 (excluding the slack-related part) in such a way as to cover the bendable range of the bending angle of the bending portion 7, but may alternatively store operation parameters which determine the operating characteristics.

That is, the storage unit 14 may store operation parameter information including the slope of the bending angle $\theta b$ vs. the rotation angle $\theta 1$ as defined by coordinate positions P1 to P2 (A3-A5) in FIG. 8, similarly the slope defined by the coordinate positions P4 to P5 (A11), and that part of operating characteristics which is attributable to a restoring force and the like and defined by coordinate positions P2 to P3 (A6-A8) and P5 to P6 (A11).

According to the present embodiment, the storage unit 14 prestores information about operating characteristics related to the action of the bending portion 7 to return in an original direction when the bending portion 7 is bent in an opposite direction after being bent in a predetermined angle, as reference information (coordinates P2 to P3 (A6-A8) and P5 to P6 (A11) in the concrete example in FIG. 8). The bending angle detection unit 12 estimates and thereby detects the corresponding bending angle from the rotation angles of the motors 37a and 37b by referring to the reference information.

In this way, according to the present embodiment, since the reference information is prestored, even if a sensor to sense the bending angle is not provided, the bending angle can be detected (estimated) more accurately from the rotation angles of the motors 37a and 37b than conventional examples in which no such reference information is stored.

Besides, the storage unit 14 also stores information about a correlation between the torque T and the bending angle $\theta b$ and information about the threshold Tth used for determination of slack.

Actually, the wires 8*a* and 8*b* become slack under the influence of flexed shape and the like of the flexed insertion portion 6, causing the rotation angle θ1 and the bending angle θb to deviate from the operating characteristics stored in the storage unit 14 depending on the usage situation. Thus, according to the present embodiment, the presence or absence of slack is detected, and if there is any slack, the information about operating characteristics used for driving to bend is changed (corrected).

Suppose, for example, a drive to bend command is inputted asking the control unit 11 to reciprocate the bending portion 7 in a predetermined direction and an opposite direction using the motor 37*a*. If the control unit 11 drives and rotates the motor 37*a* in response to the command input, the rotation angle θ1 of the motor 37*a* and the bending angle 8*b* change, for example, from A1 to A2, and to A3-A5, . . . A12, A13 in FIG. 8 due to slack of the wires 8*u* and 8*d*.

Consequently, the rotation angle θ1 shifts, for example, in a horizontal direction by an angle a in a part indicated by A12 in FIG. 8 or by an angle b, and a change is made to shift the information about operating characteristics according to the shift, for example, in the horizontal direction. In this way, if the information about operating characteristics has hysteresis characteristics whereby operating characteristics change depending on previous driving conditions, the information about operating characteristics is changed so as to reflect the hysteresis characteristics.

Figure 6:
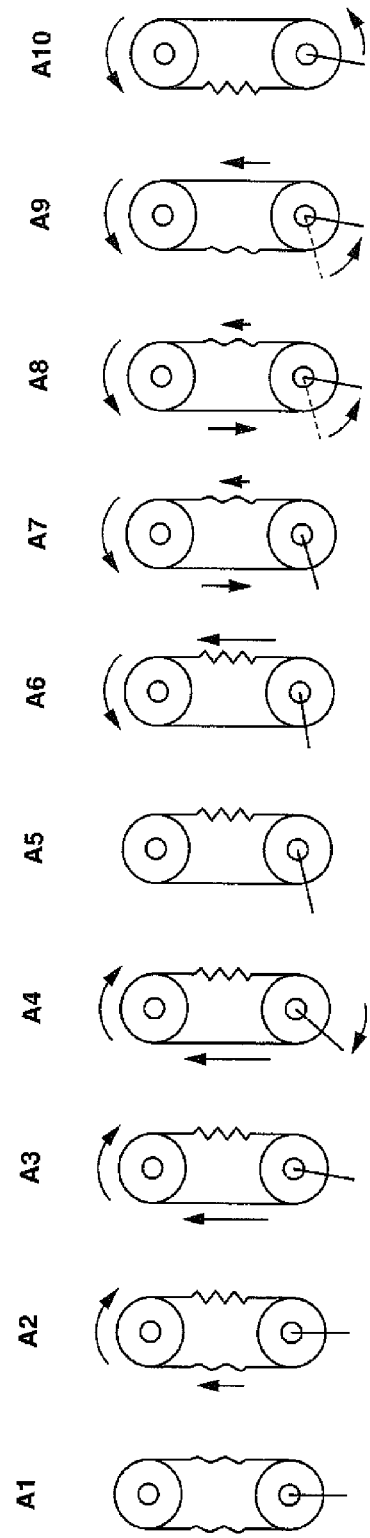
FIG. 6 is a diagram showing typical bent states when the bending portion is driven to bend by a motor using the model in FIG. 5.

Typical states of the bending angle in the parts represented by A1, . . . A13, A14 in FIG. 8 are shown in FIG. 6. FIG. 6 shows A1 to A10.

The endoscope system 1, which is a medical system configured as described above, is installed on the endoscope 2, which is a medical instrument. The endoscope system 1 includes the bending portion 7, the driving unit 9, and the control unit 11, where the bending portion 7 is a movable portion made up of the bending pieces 34 which are a plurality of pivotally coupled movable members and configured to allow an angle to be changed within a predetermined angular range in at least one plane, the driving unit 9 constitutes an actuator installed on the endoscope 2 and configured to drive the bending portion 7 so as to change the angle of the bending portion 7 when the wires 8*a* and 8*b* coupled to the bending portion 7 are pulled, and the control unit 11 is a control unit configured to perform drive control of the driving unit 9.

Also, the endoscope system 1 includes the slack detection unit 13 configured to detect a driving condition as to whether or not the wires 8*a* and 8*b* are slack, the slack adjustment unit 15 configured to adjust the slack of the wires 8*a* and 8*b* based on a detection result produced by the slack detection unit 13 as to whether or not the wires 8*a* and 8*b* are slack, and the calibration button 15*a* serving as a slack adjustment command input unit used to input a command to adjust the slack of the wires 8*a* and 8*b* to the slack adjustment unit 15.

When a command to adjust the slack is inputted, the slack adjustment unit 15 adjusts the slack in two mutually opposite directions so as to achieve a predetermined state of adjustment in which the wires 8*a* and 8*b* are not slack in one direction or the wires 8*a* and 8*b* have a same amount of slack in the two directions based on a detection result detected by the slack detection unit 13 regarding the slack of the wires 8*a* and 8*b* in at least the two directions when the wires 8*a* and 8*b* are pulled by the driving unit 9 so as to reciprocate the bending angle of the bending portion 7 in the two directions.

Next, overall operation according to the present embodiment will be described with reference to FIG. 4. When various parts of the endoscope system 1 are powered on, causing the control apparatus 10 to start operating, the control apparatus 10 performs an initialization process in Step S1.

In Step S1, the endoscope 2 is set to a neutral or initial state in which the insertion portion 6 is straight, i.e., the bending portion 7 is not bent. In the initial state, normally the angle around an approximate center of the predetermined angular range in which the insertion portion 6 is bendable is 0. The control apparatus 10 sets the rotation angles θ1 of the motors 37*a* and 37*b* in the up-and-down direction and left-and-right direction detected by the encoders 38*a* and 38*b* and the bending angle 8*b* of the bending portion 7 to 0. Subsequently, the control apparatus 10 waits for a command input.

In Step S2, the control unit 11 of the control apparatus 10 determines whether or not a slack adjustment command has been inputted via the calibration button 15*a*.

If a slack adjustment command has been inputted, the slack adjustment unit 15 of the control apparatus 10 performs a slack adjustment process in Step S3, and then the flow goes to Step S4. The operating characteristics to be stored in the storage unit 14 are corrected (calibrated) as a result of the slack adjustment process and subsequently the bending portion 7 is driven to bend based on the corrected operating characteristics.

On the other hand, if a slack adjustment command is not inputted, the flow goes to a process in Step S4 by bypassing the process in Step S3.

The process in Step S3 will be described later with reference to FIG. 9. In Step S4, the surgeon inputs a bend command using the joystick device 16*a*. Specifically, the surgeon tilts the joystick 39 by a desired bending angle in a desired bending direction.

Consequently, as shown in Step S5, based on the bending direction and the bending angle specified by the inputted command and with reference to the information about operating characteristics (for the driving condition) at the current time point in the storage unit 14, the control unit 11 of the control apparatus 10 calculates rotation directions (driving direction), torque (amounts of driving force), and rotation angles in and with which the motors 37*a* and 37*b* (hereinafter collectively referred to as the motors 37) should be rotated.

Figure 4:
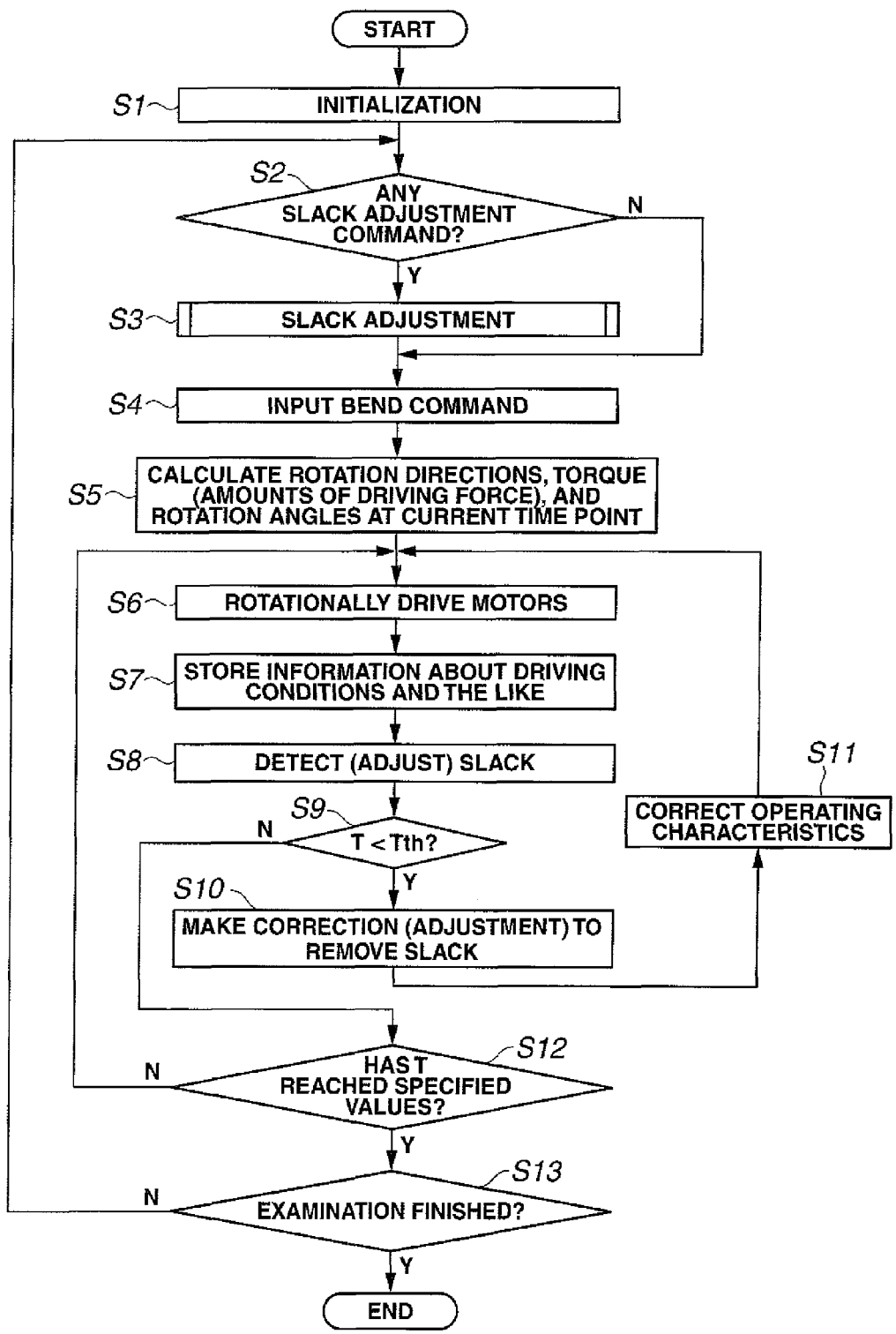
FIG. 4 is a flowchart showing an overall control procedures carried out by the control unit according to the first embodiment.

Incidentally, at the current stage, the driving condition at the current time point correspond to the driving condition in the initial state, but a bend command may be inputted under a driving condition different from that in the initial state depending on the control loop in FIG. 4. In that case, the rotation directions, the torque, and the rotation angles are calculated with reference to the information about operating characteristics corrected before the current driving condition is established. The calculated torque and rotation angles are used as specified values or target values in driving to bend.

Next, in Step S6, the control unit 11 rotationally drives the motors 37 so as to achieve the calculated torque and rotation angles. Also, as shown in Step S7, the correction unit 13*a* of the slack detection unit 13 monitors the driving condition (rotation angles and torque) of the motors 37 constituting the driving unit 9 and the operating condition (bending angle) of the bending portion 7, for example, at a certain period and stores the resulting information in the storage unit 14 in time sequence. Alternatively, the information may be stored in the storage unit 14 in time sequence together with time information rather than at a certain period.

Also, as shown in Step S8, the slack detection unit 13 detects slack. Specifically, as shown in Step S9, the slack detection unit 13 makes a comparison to determine whether or not the absolute values of the torque T detected by the torque detection unit 12*b* are less than the threshold Tth (Tth>0).

If it is detected that the absolute values of the torque T are less than the threshold Tth, since there is slack, the slack detection unit 13 makes a correction (adjustment) in Step S10 to remove the slack. Specifically, the correction unit 13a of the slack detection unit 13 rotationally drives the motors 37 as-is via the control unit 11.

Also, in Step S11, the correction unit 13a corrects the values of the rotation angles calculated in Step S5 by the amounts of the rotation angles used for slack removal in Step S10 and thereby corrects the information about the operating characteristics in the storage unit 14 to be referred to. The correction can be made with high accuracy by referring to the information stored in time sequence in Step S7.

Subsequently, the flow returns to a process in Step S6. In this way, if there is slack, (the correction unit 13a of) the slack detection unit 13 performs drive control so as to remove the slack and corrects (changes) the information about operating characteristics by an amount corresponding to the slack. In this case, since information about the driving conditions of the motors 37 and operating conditions of the bending portion 7 (specifically, information about rotation angles of the motors 37 and bending angle of the bending portion 7) is stored in time sequence in Step S7, corrections can be made reliably at each moment.

Once the slack is removed in this way, the torque T (in absolute value) of the motors 37 changes as the motors 37 rotate, and when the threshold Tth is exceeded, the flow goes to processes in Steps S9 to S12. In Step S12, the bending angle detection unit 12 determines whether or not the detected torque T has reached the specified values, i.e., the torque T calculated in Step S5.

If the detected torque T has not reached the specified values, the flow returns to the process in Step S6.

On the other hand, if the detected torque T has reached the specified torque values, the flow goes to a process in Step S13, where the control unit 11 determines whether or not a command to finish endoscopy with the endoscope 2 has been inputted.

If a command to finish endoscopy has not been inputted, the flow returns to a process in Step S2, and then Step S2 and subsequent steps are carried out. On the other hand, if a command to finish endoscopy has been inputted, the process in FIG. 4 is finished.

According to the present embodiment, since a control process described above is performed, if the wires 8a and 8b become slack, the slack can be detected appropriately through comparison with the threshold Tth of the torque T. Consequently, the slack is removed, and even if actual operating characteristics deviate from preset operating characteristics by the amount corresponding to the slack, the operating characteristics are corrected in time sequence.

Thus, according to the present embodiment, even if deviations should occur between the rotation angles of the motors 37 on the side of driving means and the actual bending angle of the bending portion 7, the bending portion 7 can be driven to bend accurately by correcting the slack.

Also, according to the present embodiment, even if the wires 8a and 8b are pulled and relaxed repeatedly, the slack adjustment in Step S3 of FIG. 4 makes it possible to drive to bend the bending portion 7 accurately by adjusting the slack appropriately.

Also, the present embodiment is widely applicable to cases in which no sensor to sense the bending angle of the bending portion 7 is provided.

In the flowchart of a control method according to the present embodiment in FIG. 4, if it is found in Step S13 that the examination has not been finished, the flow returns to the process in Step S2. Therefore, the flowchart in FIG. 4 provides the following control method.

A control method for controlling operation of an actuator configured to drive a bending portion 7 so as to change a bending angle of the bending portion 7 via pulling operation of the wires 8a and 8b includes Step S8 (and S9) which corresponds to a slack detection step of detecting a driving condition as to whether or not the wires 8a and 8b are slack, and Step S10 which corresponds to a first slack adjustment step of adjusting slack of the wires 8a and 8b based on a detection result produced by the slack detection step S8 as to whether or not the wires 8a and 8b are slack.

Also, the control method includes Step S2 which corresponds to a command input step of inputting a command to adjust the slack of the wires 8a and 8b, and Step S3 which corresponds to a second slack adjustment step of adjusting the slack of the wires 8a and 8b to a predetermined state of adjustment with a known amount of slack based on the command to adjust the slack of the wires 8a and 8b inputted by Step S2, based on a detection result produced by Step S8 regarding the slack of the wires 8a and 8b in at least two mutually opposite directions when the wires 8a and 8b are pulled so as to reciprocate the bending angle of the bending portion 7 in the two directions. Consequently, even if the wires 8a and 8b are pulled and relaxed repeatedly, drive control for changing the bending angle of the bending portion 7 can be performed accurately.

Next, operation of the present embodiment will be described more specifically. In so doing, to illustrate operation of the bending portion 7 in a simplified manner, the left side of FIG. 5 including the driving unit 9 side and the bending portion 7 side are represented by a model on the right side. On the left side of FIG. 5, the pulleys 36a and 36b and the motors 37a and 37b in FIG. 3 are represented by a pulley 36 and a motor 37, respectively.

Also, the wires 8a and 8b represent the wires 8u and 8d or the wires 8l and 8r. Thus, this configuration assumes a special case in which the driving unit 9 and the bending portion 7 are bent in a plane in the up-and-down direction or left-and-right direction, but the configuration is also applicable to a plane in another direction. Also, in the model on the right side of FIG. 5, the pulley 36 on the side of the driving unit 9 is represented by a pulley 36', the actual bending portion 7 is modeled virtually by a bending pulley 7', and the bending direction of the bending portion 7 is indicated by a thick, bending direction line L.

Figure 5:
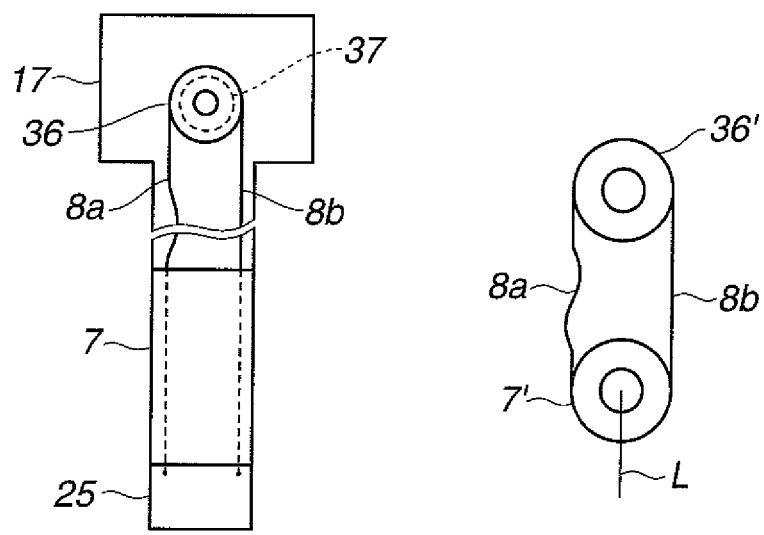
FIG. 5 is a diagram showing a model with a simplified bending portion and a driving unit.

FIG. 6 shows typical bent states A1 to A10 which result when an operation of rotating the pulley 36 by a predetermined angle at constant power and then by a predetermined angle in an opposite direction is repeated by rotationally driving the motor 37 in FIG. 5.

Figure 7:
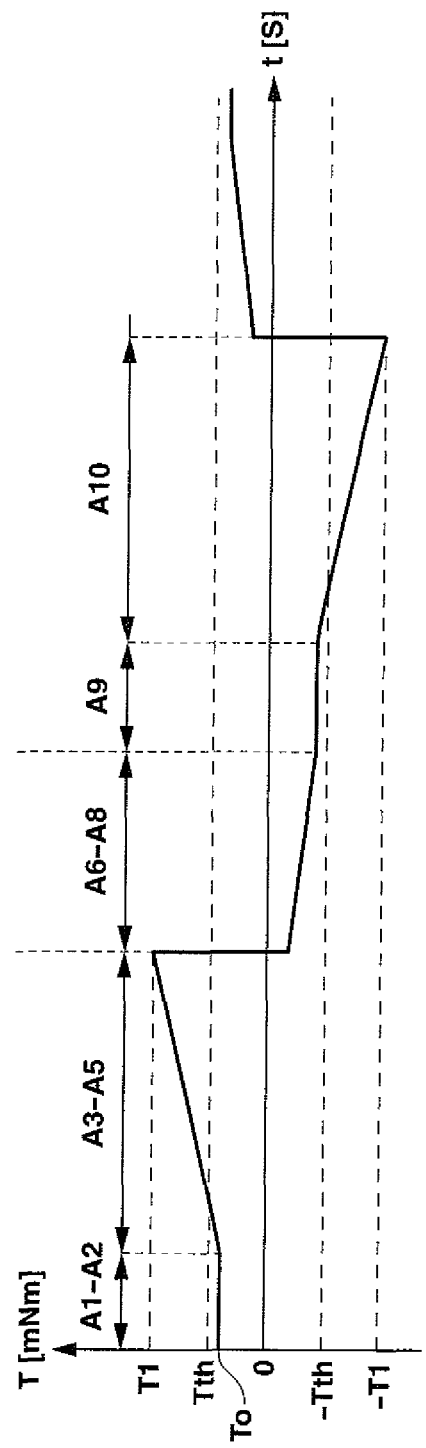
FIG. 7 is a diagram showing a time variation of torque when an operation of driving to bend the bending portion to one bending angle once and then to a bending angle in an opposite direction is repeated by rotating the motor using the model in FIG. 5.

Also, FIG. 7 shows torque T generated when the motor 37 pulls the wires 8a and 8b during the above operation. FIG. 8 shows an example of actual operating characteristics expressed by coordinates of the rotation angle $\theta 1$ and the bending angle $\theta b$ corresponding to the operation.

A1 in FIG. 5 represents a bent state (initial state in which the bending portion 7 is straight and is not bent) at the start of operation. Starting from A1, the pulley 36 is rotated clockwise by the motor 37 as indicated by A2. In A1, the wire 8a is slack. When the pulley 36 is rotated clockwise (in the forward direction) by the motor 37, the slack is removed from the wire 8a.

That is, as shown in FIGS. 7 and 8, in an A1-A2 process of transition from A1 to A2, the bending angle $\theta b$ does not change relative to the rotation angle $\theta 1$. In FIG. 7, To represents a torque value which results when the pulley 36 is rotationally driven at constant power. On the other hand, T1 represents a torque value corresponding to a specified value of the bending angle.

The slack detection unit 13 compares the detected torque T with the threshold Tth. When a result of the comparison is T<Tth, the slack detection unit 13 determines that there is slack, and rotates the motor 37 so as to remove the slack.

After A2 in which the slack has been removed, if the motor 37 rotate further, the bending angle θb starts to change as well. Actual position (of the rotation angle) according to the operating characteristics in A2 is sensed by the encoder 38. After passing A2, the torque T increases from the initial torque To in A1, and when the threshold Tth is exceeded, the slack detection unit 13 determines that the slack has been removed (i.e., there is no slack).

Subsequently, the bending angle θb changes along with the rotation angle θ1 of the motor 37, and after passing A3 and A4, i.e., an A3-A5 process in FIG. 7, reaches a predetermined bending angle θb1 in A5 (coordinate position P2). At this point, the rotation angle is, for example, θ11 and the torque T becomes torque T1 set according to the bending angle θb1 (FIG. 7).

Subsequently, if a command for a bending angle −θb1 in an opposite direction is inputted, the motor 37 starts to rotate in the opposite direction. In this case, as shown in FIG. 6, the wire 8b has accumulated considerable slack in A5, and an elastic member such as a sheathing tube of the flexible portion 26 with flexibility generates a restoring force tending to return the bending portion 7 to a straight state (from a bent state). Due to the restoring force, the bending portion 7 in the bent state acts to reduce the bending angle θb. Also, since the wires 8a and 8b are passed through the flexible portion 26, a frictional force acting on the wires 8a and 8b also works.

Consequently, the rotation angle θ1 and the bending angle θb change according to characteristics corresponding to a mixture of the restoring force and the frictional force, i.e., characteristics shown in A6 to A8 in FIGS. 7 and 8. During this change, the values of the bending angle θb corresponding to changes in the rotation angle θ1 are estimated by referring to the information in the storage unit 14.

Also, during the transition of A6-A8, since the restoring force initially has a greater impact, the absolute value of the torque T approaches the initial value To from a value smaller than the initial value To, as shown in FIG. 7.

When the restoring force becomes balanced with the frictional force, the impact of the restoring force practically disappears in A8. If slack exists in A8, the bending angle θb does not change in A9 even if the rotation angle θ1 of the motor 37 changes until the slack is eliminated.

When the state of A9 ends, the bending angle θb changes with changes in the rotation angle θ1 and the absolute value of the torque T exceeds the threshold Tth. In A9 where the absolute value of the torque is less than the threshold Tth, a correction is made by removing an amount corresponding to the rotation angle as slack.

When the absolute value of the torque T exceeds the threshold Tth, it is determined that the slack has been removed (i.e., there is no slack), and the bending angle θb changes with changes in the rotation angle θ1 as indicated by A10. In this way, the rotation angle θ1 and the bending angle θb change with a slope shown in A10.

A10 corresponds to A3-A5 described above. When the bending angle −θb1 is reached, the motor 37 stops rotating. At this point, the rotation angle is −θ11′.

Then, if a command for the bending angle θb1 has been inputted, after A11 corresponding to A6-A8, the slack is removed in A12 corresponding to A9. Also, a correction is made by the amount corresponding to the slack.

Subsequently, the bending angle θb1 is reached through a process in A13 indicated by a dotted line and corresponding to A3-A5. In this case, a rotation angle θ12 corresponding to the bending angle θb1 deviates by b from the rotation angle in A3-A5. Then, the operating characteristics used for driving to bend are changed by an amount equivalent to the amount of deviation. Furthermore, when the motor 37 is rotated in the opposite direction, the same process is repeated after a process in A14 indicated by a dotted line in FIG. 8.

According to the present embodiment, as described above, information about operating characteristics which relates the rotation angle θ1 and the bending angle θb to each other as shown in FIG. 8 as well as information about operating characteristics which associates the torque T and the bending angle θb with each other (not shown) are stored in the storage unit 14, and when the wires 8a and 8b become slack, drive control is performed so as to remove the slack and the information about operating characteristics used for driving to bend is corrected in consideration for the impact of the slack.

Next, a slack adjustment process in Step S3 of FIG. 4 will be described with reference to FIG. 9. As described above, a slack adjustment process is started when a slack adjustment command is inputted via the calibration button 15a. First, in Step S21, the slack adjustment unit 15 sets the bending direction for slack adjustment via the control unit 11. The bending direction can be set in advance via the command input unit 16 or the like.

Alternatively, the user may set a specific bending direction in which to input a bend command before the slack adjustment. For the sake of simplicity, it is assumed here that the bending direction is set to the up-and-down direction or left-and-right direction.

Next, in Step S22, via the control unit 11, the slack adjustment unit 15 rotates the motor 37 in a predetermined rotation direction corresponding to the specific bending direction for slack adjustment and in a reverse rotation direction opposite to the rotation direction, rotating the motor 37 back and forth within an appropriate angular range.

The appropriate angular range may be set at a value larger than a maximum angular error caused by the slack of the wires 8a and 8b (and within a predetermined range which will allow the bending portion 7 to be bent). Also, the slack adjustment unit 15 operates the slack detection unit 13 via the control unit 11.

In the following description, it is assumed that reciprocating motion is performed a single time, but the reciprocating motion may be performed multiple times to calculate an average rotation angle which corresponds to a boundary between a state in which slack exists and a state free of slack (or a state in which slack has been removed), based on the multiple times of reciprocation. By performing the reciprocating motion multiple times and using the average rotation angle which corresponds to the boundary between a state in which slack is determined to be present and a state in which slack is determined to be absent, it is possible to detect and adjust slack with higher accuracy.

Figure 10:
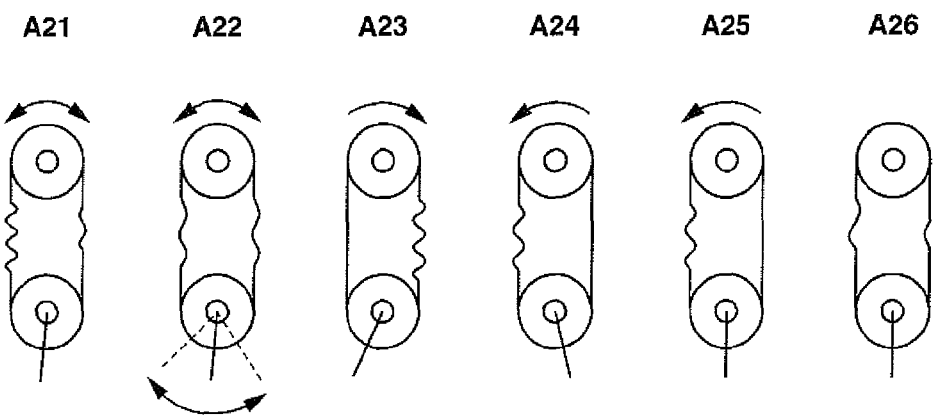
FIG. 10 is an explanatory diagram showing the process in FIG. 9 using a model.
Figure 11:
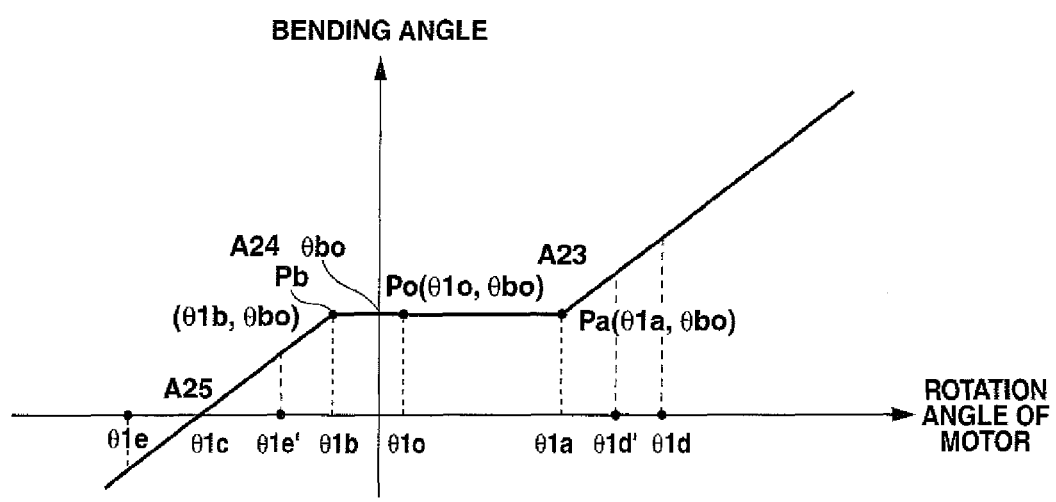
FIG. 11 is an explanatory diagram showing details of the process in FIG. 9 using the rotation angle and the bending angle.

In FIG. 10, A21 shows a state just before the start of Step S21. In the state of A21, the motor 37 is rotated (forward), for example, in a direction indicated by an arrow, and then rotated in the opposite direction. That is, as shown in A22, the motor 37 is rotated back and forth within a predetermined angular range. In FIG. 11, the predetermined angular range is defined by θ1d and θ1e.

In Step S23, the slack detection unit 13 detects the torque T which results when the motor 37 is driven in the rotation directions indicated in Step S22 and detects the presence or absence of slack based on whether or not the absolute value of the torque T is less than the threshold Tth.

Next, in Step S24, the slack detection unit 13 detects rotation angles of the motor 37 in the two directions when the motor 37 is rotationally driven in the rotation directions indicated in Step S23, beginning with a state in which slack exists and ending with a state in which slack removal is complete.

Suppose, for example, the rotation angle of the motor 37 and the bending angle of the bending portion 7 in the driving condition of the endoscope 2 before the start of adjustment operation are represented by a coordinate position Po ($\theta 1o$, $\theta bo$) in FIG. 11. Then, rotation angles $\theta 1a$ and $\theta 1b$ at respective coordinate positions Pa ($\theta 1a$, $\theta bo$) and Pb ($\theta 1b$, $\theta bo$) are detected, where at the coordinate position Pa ($\theta 1a$, $\theta bo$), the original slack is removed by slack produced by forward rotation of the motor 37 from the coordinate position Po and at the coordinate position Pb ($\theta 1b$, $\theta bo$), the original slack is removed by slack produced by reverse rotation of the motor 37. The rotation angles $\theta 1a$ and $\theta 1b$ correspond to rotation angles in a slack-free state in which the absolute value of the torque T matches the threshold Tth. The slack adjustment unit 15 acquires information about the rotation angles $\theta 1a$ and $\theta 1b$ detected by the slack detection unit 13.

In FIG. 10, A23 shows a state at the coordinate position Pa in FIG. 11 and A24 shows a state at the coordinate position Pb in FIG. 11.

Next, in Step S25, based on the information about the rotation angles $\theta 1a$ and $\theta 1b$ in the two directions, the slack adjustment unit 15 corrects (adjusts) the driving condition which correlates the rotation angles and bending angle at the coordinate position Po with each other before the slack adjustment.

Specifically, the driving condition is corrected to a predetermined driving condition or a predetermined state of adjustment which will subsequently allow accurate bending operation, by taking into consideration that there is an amount of slack equivalent to $|\theta 1a-\theta 1b|$ during rotation in a forward direction and rotation in a reverse direction under the driving condition at the coordinate position Po.

For example, the unadjusted driving condition shown in A21 of FIG. 10 is adjusted (set) to a predetermined state of adjustment such as a state of adjustment in which slack has been removed (for driving) in the forward direction as is the case at the coordinate position Pa ($\theta 1a$, $\theta bo$) corresponding to A23 or a state of adjustment in which slack has been removed (for driving) in the reverse direction as is the case at the coordinate position Pb ($\theta 1b$, $\theta bo$) corresponding to A24.

Then, to reflect the state of adjustment, the information about the operating characteristics of (the motors 37a and 37b constituting) the driving unit 9 and the bending portion 7 (bending angle) stored in the storage unit 14 is corrected.

Under the driving condition at the coordinate position Pa, the bending operation can be performed in a state free of slack in the case of bending in a specific bending direction corresponding to forward rotation.

On the other hand, under the driving condition at the coordinate position Pb, the bending operation can be performed in a state free of slack in the case of bending in a bending direction opposite to the bending direction at the coordinate position Pa.

That is, since the rotation angle at which slack is removed is detected in each direction by rotationally driving the motor 37 in mutually opposite directions to achieve a predetermined driving condition or state of adjustment, even if there are hysteresis characteristics, the impact of slack can be reduced with higher accuracy than when slack is detected only in a single direction.

Also, since under the driving condition in which a slack adjustment command is issued, the motors 37a and 37b are rotationally driven so as to pull the wires in mutually opposite directions starting from the current driving condition and slack adjustments are made by detecting a range of rotation angles corresponding to the amounts of slack generated in the two directions, even if there are hysteresis characteristics, the situation with regard to amounts of slack can be grasped quantitatively under the given driving condition and the impact of slack can be reduced subsequently, allowing accurate bending control.

In Step S26 following Step S25, the slack adjustment unit 15 determines whether or not a setting has been made by the user via the control unit 11 to return (reset) the driving condition to the initial state.

Figure 9:
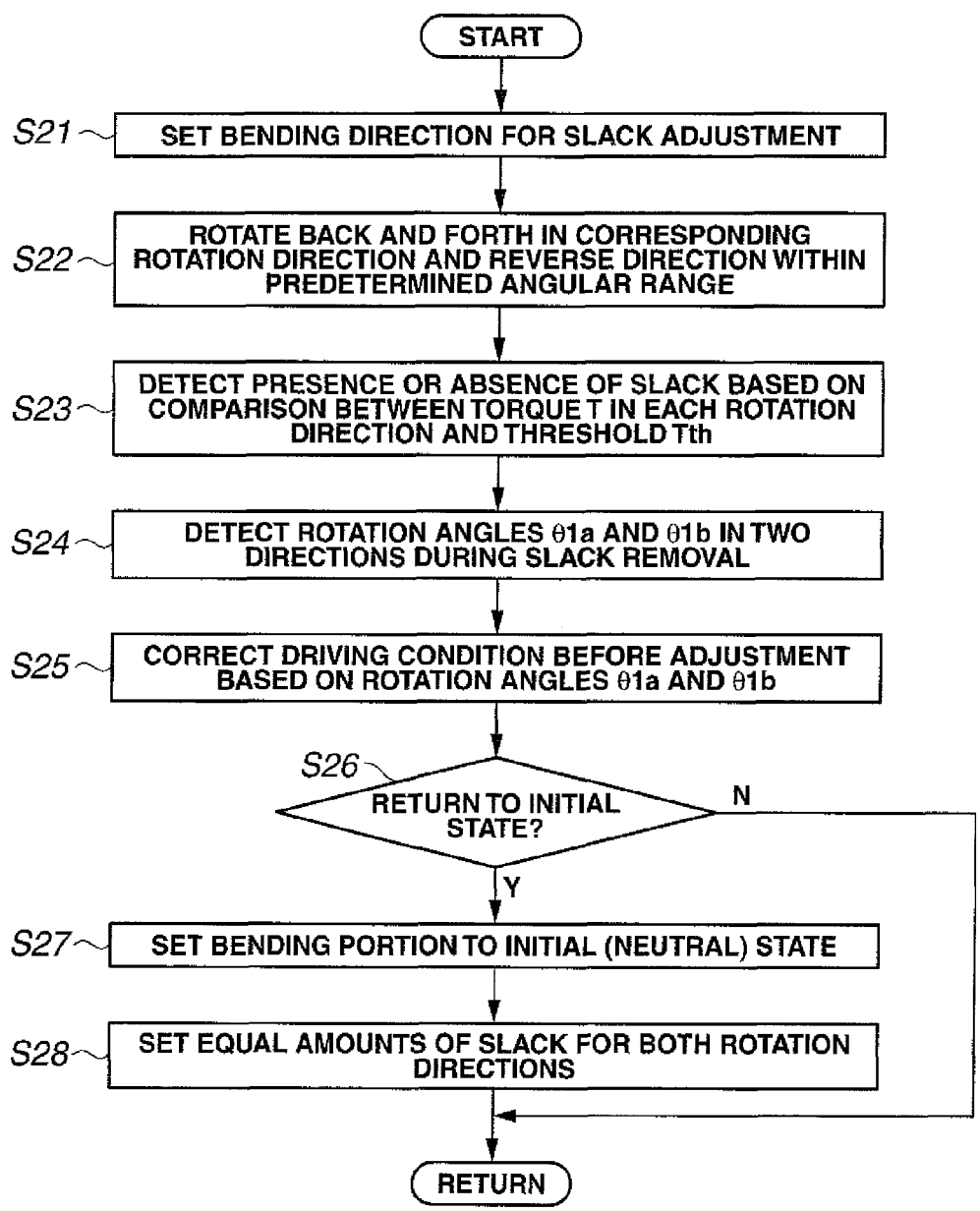
FIG. 9 is a flowchart showing a concrete example of the process of adjusting slack in FIG. 4.

If no setting has been made to return to the initial state, processes in FIG. 9 are terminated and the flow goes to a process in a next step, i.e., Step S4 in FIG. 4.

On the other hand, if a setting has been made to return to the initial state, the slack adjustment unit 15 makes a setting in Step S27 via the control unit 11 to return the bending portion 7 to the initial state. For example, in the example shown in FIG. 11, the state of A24 is established at the coordinate position Pb and then the motor 37 is rotated along A25 to a rotation angle $\theta 1c$ (close to the initial state) at which the bending angle $\theta b$ becomes 0. In the initial state, the bending portion 7 is freed from being driven by the motors 37a and 37b and the bending angle is close to 0.

In Step S28 next, the slack adjustment unit 15 makes an adjustment to equalize slack in the two rotation directions as shown in A26 in FIG. 10.

A26 shows how an amount of slack equivalent to $|\theta 1a-\theta 1b|/2$ is set to exist in each of the two rotation directions if the rotation angles of the motors 37a and 37b (corresponding to a specific bending direction in the initial state of the bending portion 7) have an amount of slack equivalent to $|\theta 1a-\theta 1b|$ in the initial state.

The value of $|\theta 1a-\theta 1b|$ and the corresponding amount of slack are known from characteristics of the motors 37a and 37b and the pulleys 36a and 36b. The slack adjustment unit 15 stores the information about operating characteristics after such a slack adjustment in the storage unit 14. Incidentally, the storage unit 14 may store the amount of slack corresponding to the value of $|\theta 1a-\theta 1b|$ together with or instead of the value of $|\theta 1a-\theta 1b|$.

According to the present embodiment, since a state of adjustment with known amounts of slack is established so as to provide equal amounts of wire slack equivalent to $|\theta 1a-\theta 1b|/2$ in two mutually opposite rotation directions, even if there are hysteresis characteristics due to wire slack, a relationship between the rotation angle of the motor (pulley) in FIG. 8 and the corresponding bending angle can be determined accurately.

In this way, according to the present embodiment, since the amounts of wire slack in the initial state are calibrated to known values (more specifically, equal amounts of slack) in two rotation directions (corresponding to the specific bending direction), subsequent drive control of bending can be performed accurately.

Incidentally, in Step S28, if the slack adjustment operation described above is performed in a state close to the initial state, slack information (specifically, information corresponding to the amount of slack |θ1a-θ1b|) acquired by the slack adjustment operation such as described above may be used as it is.

Regarding a state of the bending angle far from the initial state, such as a state of the bending angle after bending greatly from the initial state, the processes of Steps S22 to S25 and S28 may be performed after the bending angle is set to the initial state.

Although it has been stated above that the slack adjustment unit 15 adjusts the initial state such that equal amounts of slack will exist in two rotation directions, a setting may be made to provide no slack in one rotation direction, and a known amount of slack (amount of slack equivalent to |θ1a-θ1b|, in the above example) in the other rotation direction (or vice versa).

The adjustment to a predetermined state of adjustment in which equal amounts of slack exist in two rotation directions as described in relation to the initial state may also be applied to states other than the initial state. In either case, in the present embodiment, a state of adjustment with known amounts of slack is established.

Although the slack adjustment process has been described in FIG. 9, assuming that the slack in the bending portion 7 is adjusted in a specific bending direction out of the up-and-down direction and left-and-right direction, when the bending portion 7 is bendable both in the up-and-down direction and left-and-right direction, the slack adjustment process may be performed in each of the up-and-down direction and left-and-right direction. If the bending portion 7 is bendable only in the up-and-down direction or left-and-right direction, the slack adjustment process is performed only in the up-and-down direction or left-and-right direction.

As a variation of the flowchart processes in FIG. 9, when inputting a slack adjustment command, the user may be allowed to specify a rotation angle and/or bending angle near the angle of actual slack adjustment, and then the slack adjustment can be carried out near the specified rotation angle and/or bending angle.

Normally, when a slack adjustment command is inputted, the processes of Steps S21 to S25 in FIG. 9 are performed near where the slack adjustment command is inputted, but slack adjustments may be allowed to be carried out near a rotation angle and/or bending angle other than the angles at which the slack adjustment command is inputted. In this case, it is advisable that the user is allowed to choose to carry out slack adjustments in a state close to the initial state.

In this way, according to the present embodiment, since the slack adjustment process shown in FIG. 9 is performed, even when the bending portion 7 is driven to bend by pulling and relaxing the wires 8a and 8b repeatedly, slack adjustments can be carried out by allowing for (reflecting) hysteresis characteristics, in other words, by reducing an impact of hysteresis characteristics sufficiently. Thus, the present embodiment makes it possible to drive to bend the bending portion 7 accurately.

In the present embodiment, calibration is performed by bending the bending portion 7 in mutually opposite bending directions, detecting the range of rotation angles in which the slack produced in the two directions are reduced, i.e., detecting the amounts of slack (equivalent) quantitatively, and making adjustments so as to correct for the impact of the slack based on the detected amounts of slack.

Thus, the present embodiment allows a driving to bend mechanism with hysteresis characteristics to be calibrated more accurately than when slack is adjusted or calibrated only in one direction.

Also, not only in the initial state before the bending portion 7 is actually driven to bend, but also when the bending portion 7 is actually driven to bend, an input of a slack adjustment command causes the amounts of slack in the current driving condition to be detected (grasped), making it possible to carry out subsequent driving to bend accurately.

Also, since there is no need for a sensor configured to detect tension acting on the wires 8a and 8b, the present embodiment is widely applicable to existing endoscopes not provided with such a sensor.

Incidentally, if the bending portion 7 is capable of bending in a single bending direction such as an upward direction from a neutral state such as a straight state, the slack setting in Step S28 of FIG. 9 may be configured as follows.

Since the bending portion 7 is bendable only in the upward direction in the neutral state, to improve responsivity to a bend command for upward bending, slack may have been removed in the upward direction. On the other hand, a bend command for bending in any of multiple bending directions is accepted, Step S28 of FIG. 9 ensures equal responsivity in all the bending directions. However, if the frequency of bending varies among different directions, higher responsivity may be ensured preferentially in the frequently used bending direction than the other bending directions. Also, responsivity in a specific bending direction may be ensured at the user's option.

Although the slack adjustment unit 15 and the slack detection unit 13 have been described above as being separate components, one of the slack adjustment unit 15 and the slack detection unit 13 may be configured to include (functions of) the other.

Second Embodiment

Figure 12:
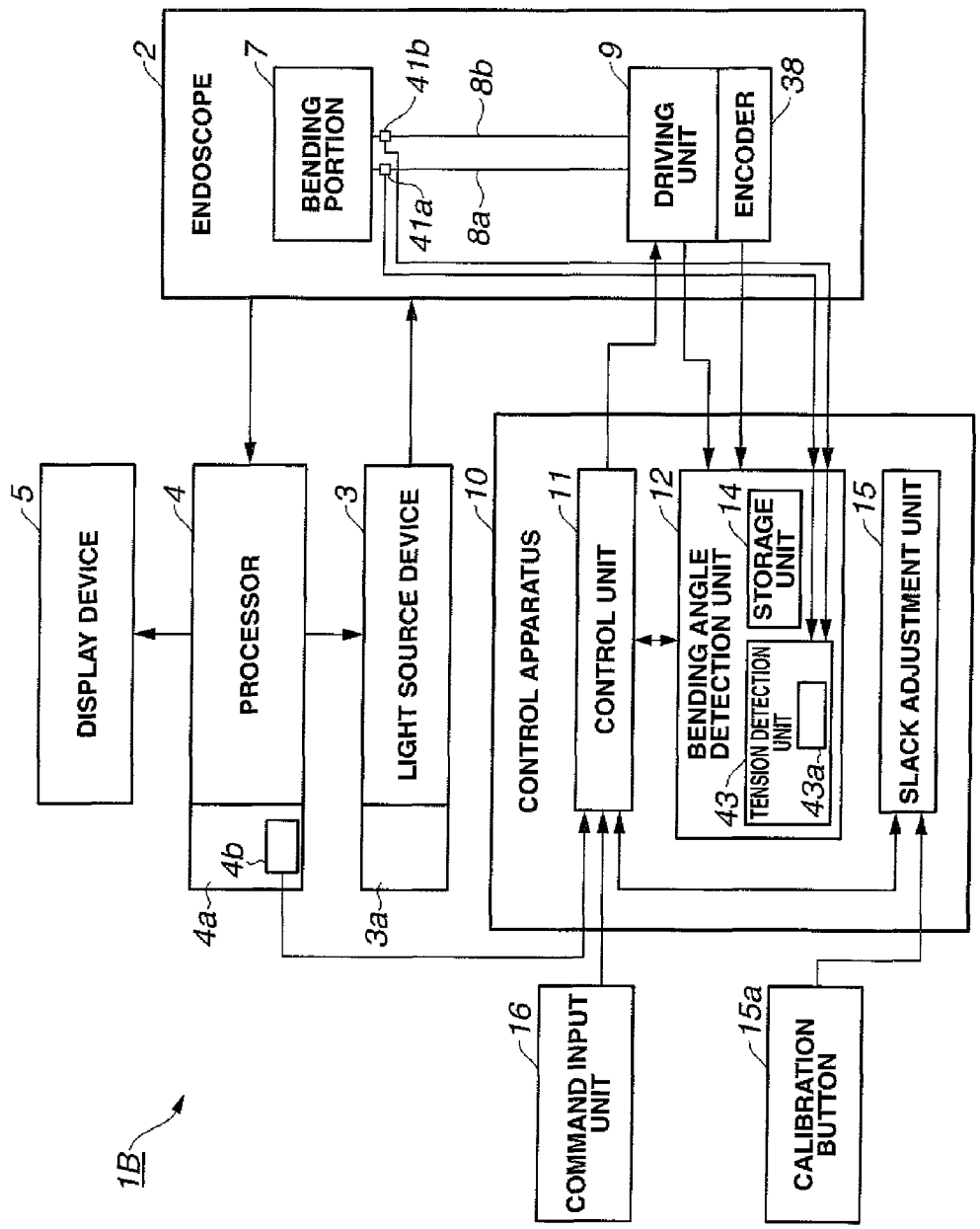
FIG. 12 is a block diagram showing an overall configuration of an endoscope system according to a second embodiment of the present invention.

FIG. 12 shows an endoscope system 1B according to a second embodiment of the present invention. According to the present embodiment, tension sensors 41a and 41b are provided to sense tension (load) acting on one or more pairs of respective wires 8a and 8b of the endoscope 2. Note that there are one or two pairs of wires 8a and 8b. Also, there are one or two pairs of tension sensors 41a and 41b.

Also, the bending angle detection unit 12 of the control apparatus 10 includes a tension detection unit 43 configured to detect the tension acting on the wires 8a and 8b based on sensing signals from the tension sensors 41a and 41b and thereby detect the bending angle of the bending portion 7. Incidentally, the bending angle detection unit 12 may detect the bending angle of the bending portion 7 with reference to information about the rotation angles of the motors of the driving unit 9 as well.

Also, whereas the first embodiment includes the slack detection unit 13 configured to detect whether or not there is slack based on detected values of the torque T, in the present embodiment, the tension detection unit 43 functions as a slack detection unit 43a configured to detect whether or not there is slack based on detected values of tension.

According to the present embodiment, the slack detection unit 43a of the tension detection unit 43 detects the presence or absence of slack based on whether or not the detected values of the tension acting on the wires 8a and 8b are less than the absolute value of a tension threshold. In other words, by detecting the tension acting on the wires 8a and 8b, the slack detection unit 43a detects loads on the wires 8a and 8b and detects whether or not the wires 8a and 8b are in a driving condition with slack. The rest of the configuration is the same as that of the first embodiment.

Thus, description of the operation of the first embodiment generally applies to the present embodiment except that the bending angle of the bending portion 7 is detected by the tension detection unit 43 (or by the tension detection unit 43 and the encoder 38) and that the slack of the wires 8a and 8b is detected based on the values of tension detected by (the slack detection unit 43a) of the tension detection unit 43 instead of the values of the torque T detected by the slack detection unit 13.

Figure 13:
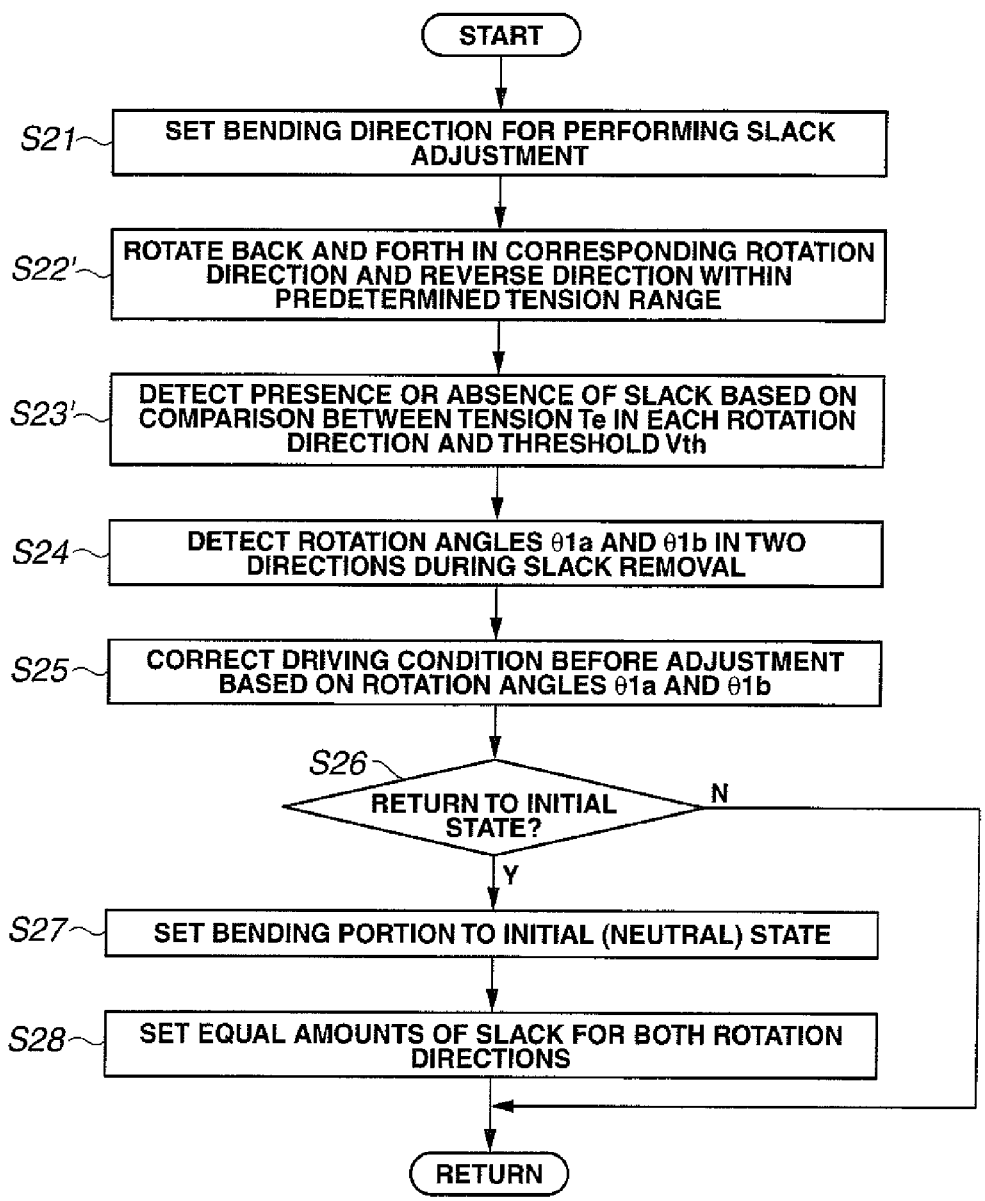
FIG. 13 is a flowchart showing a concrete example of the process of adjusting slack according to the second embodiment.

According to the present embodiment, when a slack adjustment command is inputted, a slack adjustment process is performed, for example, as shown in FIG. 13. In FIG. 13, the process of Step S23 in the slack adjustment process of FIG. 9 is replaced with the process of Step S23', which is "the process of detecting the presence or absence of slack based on whether or not a value of tension Te in each rotation direction detected by the tension sensor 41a or 41b is less than a threshold Vth (of the tension Te)."

Also, in the present embodiment, the process of Step S22 in FIG. 9 is changed slightly and the motor 37 is rotated back and forth within a predetermined tension range instead of being rotated within a predetermined angular range. The predetermined tension range is a predetermined range (−Vth−Δ to Vth+Δ) slightly wider than a threshold Vth range (−Vth to Vth), where Δ is a small positive value.

In this way, by rotating the motor 37 back and forth within the predetermined tension range, the impact of hysteresis characteristics is reduced. That is, since increasing a range of rotation back and forth increases the impact of hysteresis characteristics, the motor 37 is rotated back and forth in a region near the rotation angles at which slack adjustments are to be made and in the tension range in which the presence or absence of slack can be detected.

This makes it possible to carry out slack adjustments by reducing the impact of hysteresis characteristics. Incidentally, in the first embodiment, the motor 37 may be rotated back and forth within a predetermined torque range (−Tth−Δ to Tth+Δ) instead of being rotated within the predetermined angular range in Step S22.

When the motor 37 is rotated back and forth within the torque range, the motor 37 has a rotation angle range of θ1d' to θ1e' as shown in FIG. 11, making it possible to detect the rotation angles θ1a and θ1b described above by reducing the impact of hysteresis characteristics.

The present embodiment differs from the first embodiment in slack detection means, but achieves about the same operation and effect as those of the first embodiment.

As a variation of the present embodiment, the user may be allowed to select between detecting the presence or absence of slack based on the detected values of the torque T of the motor 37 and detecting the presence or absence of slack based on tension values detected by the tension sensors 41a and 41b configured to sense the tension acting on the wires 8a and 8b.

Also, for example, a white balance command input unit 4b for use to input a white balance command may be installed on the command input unit 4a of the processor 4 shown in FIG. 12. Then, when the white balance command input unit 4b is operated, a command signal may be inputted to the processor 4 and inputted as a slack adjustment command signal to the slack adjustment unit 15.

Consequently, in endoscopy with the endoscope system 1B, a slack adjustment process can be performed simultaneously with command input (such as white balance command input) for signal processing settings widely carried out during initialization. Since the two processes are different from each other, if the two processes are carried out simultaneously, the two can be finished in a short period of time and the need to input commands separately is eliminated. This improves operability.

Also, by carrying out slack adjustments under initial conditions, it is possible to accurately drive to bend the bending portion 7 subsequently.

Besides, the slack adjustment process may be allowed to be performed simultaneously through command input or other action from the light source device 3.

In the embodiments described above, the present invention is applied to the endoscope 2, which is an active medical instrument equipped with the bending portion 7 and an actuator configured to drive the bending portion 7 via the wires 8a and 8b, but the present invention may be applied to a treatment instrument used as such an active medical instrument.

Figure 14:
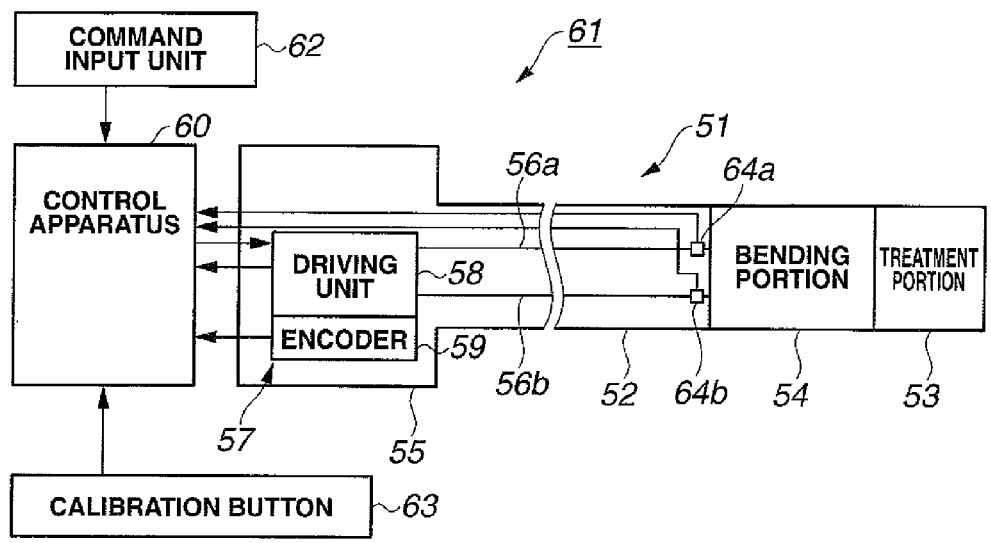
FIG. 14 is a configuration diagram of a medical system equipped with a treatment instrument according to a first variation of the second embodiment.

FIG. 14 shows a medical system 61 which uses such an active treatment instrument 51. The treatment instrument 51 includes an elongated axial portion 52, a treatment portion 53 installed at a distal end portion of the axial portion 52 and used to administer treatment, a bending portion 54 installed at a proximal end of the treatment portion 53 and configured to be bendable, and a grasping portion 55 installed at a proximal end of the axial portion 52.

The bending portion 54 is connected to a driving unit 58 of an actuator 57 in the grasping portion 55 via wires 56a and 56b passed through the axial portion 52. A rotation angle of a motor (not shown) constituting the driving unit 58 is detected by an encoder 59.

Also, the driving unit 58 and the encoder 59 are connected to a control apparatus 60. The control apparatus 60 is connected with a command input unit 62 used to input a bend command and a calibration button 63 used to input a calibration command.

The wires 56a and 56b are provided with tension sensors 64a and 64b configured to sense tension. Sensing signals from the tension sensors 64a and 64b are inputted in a tension detection unit (which corresponds to the tension detection unit 43 in FIG. 12; not shown) in the control apparatus 60.

The bending portion 54 in FIG. 14 is similar in configuration to the bending portion 7 in FIG. 2, the driving unit 58 is similar in configuration to the driving unit 9 in FIG. 2, and the control apparatus 60 is similar in configuration to the control apparatus 10 in FIG. 12.

A variation shown in FIG. 14 achieves about the same operation and effect as those of the second embodiment.

Incidentally, the present variation can be applied not only to a configuration in which the driving unit 58 constituting the actuator 57 drives the bendable, bending portion 54 via the wires 56a and 56b, but also to a case in which the driving unit 58 drives, for example, a movable portion of the treatment portion 53.

Figure 15:
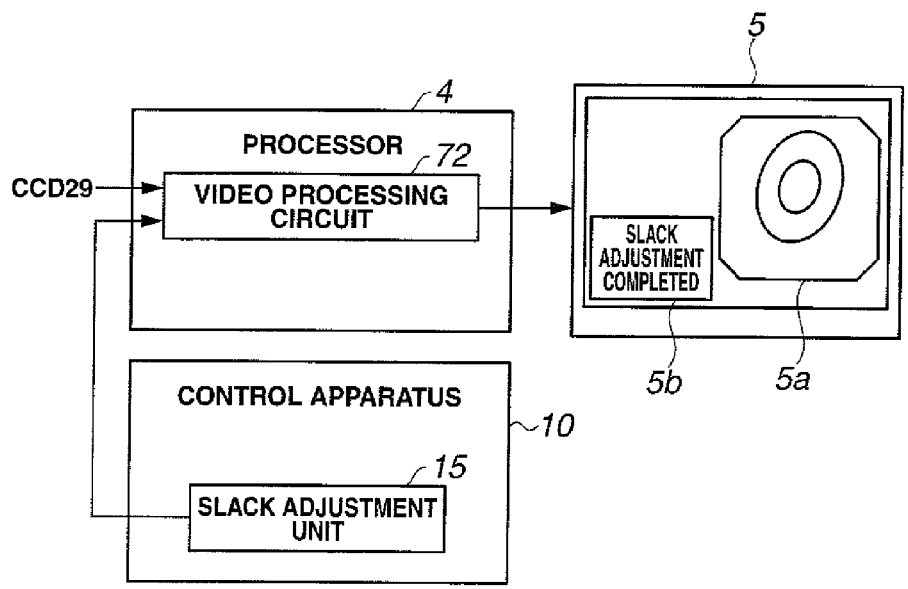
FIG. 15 is a configuration diagram showing part of a configuration according to a second variation of the second embodiment.

Also, in the embodiments and variations described above, when a slack adjustment process is further performed, the slack adjustment unit 15 of the control apparatus 10 or the like may output slack adjustment results to a video processing circuit 72 of the processor 4 as shown in FIG. 15 and the video processing circuit 72 may generate a video signal of slack adjustment results in superimposition with a video signal of endoscopic images from the image pickup device 29.

As shown in FIG. 15, using the video signal outputted to the display device 5 from the video processing circuit 72, endoscopic images are displayed in an endoscopic display area 5a on a display surface of the display device 5 and the slack adjustment results are displayed in a slack adjustment display area 5b.

Although a message "Slack adjustment completed" is displayed in FIG. 15, indicating that the slack adjustment has been completed, a message, for example, "Slack adjustment in progress" will be displayed during a slack adjustment.

This configuration allows the surgeon to check a state of slack adjustment (without shifting his/her eyes) while observing endoscopic images.

Incidentally, for example, if the first embodiment does not have the storage unit 14 configured to store information about operating characteristics or operation parameters of the driving unit 9 and the bending portion 7, control means can adjust or correct operating characteristics used to drive to bend the bending portion 7 based on results of slack adjustments.

The configuration and method for wire slack adjustment according to the present invention is widely applicable to adjustment of slack in wires in active medical instruments equipped with driving means, or an actuator, configured to change an angle of a movable portion such as the bending portion 7 via pulling of the wires.

If it is desired to finely adjust slack in wires, the slack may be adjusted finely together with a state of hysteresis characteristics by increasing the rotation range of the motor 37 or the bending angle of the bending portion 7.

Although in the embodiments described above, the motor for rotational driving is used as the actuator configured to pull the wires, other driving means such as a piezoelectric element may be used alternatively. In that case, an amount of driving and amount of driving force of the driving means such as the piezoelectric element may be used instead of the rotation angle and torque of the motor. Also, information about the amount of driving is stored in the storage unit 14 instead of information about the rotation angle.

Also, although in the above description, slack is adjusted to different states of adjustment between the case where a slack adjustment command is inputted via the slack adjustment command input unit and the case where the bending portion is driven to bend without input of any slack adjustment command, the state of adjustment of one case may be applied to the other case.

Embodiments and the like configured by combining parts of the embodiments and the like described above are also included in the present invention.

What is claimed is:

1. A medical system comprising:
 a movable portion installed in a medical instrument, made up of a plurality of pivotally coupled movable members, and configured to allow an angle to be changed within a predetermined angular range in at least one plane;
 an actuator installed in the medical instrument and including a drive shaft configured to drive the movable portion so as to change the angle of the movable portion when a wire coupled to the movable portion is pulled;
 a rotation angle detection unit configured to detect a rotation angle actually rotated with the drive shaft by the actuator;
 a control unit configured to perform drive control of the actuator;
 a slack detection unit configured to detect a driving condition as to whether or not the wire is slack;
 a slack adjustment command input unit configured to input a command to adjust the slack of the wire; and
 a slack adjustment unit configured to, when the command to adjust the slack is inputted, cause the drive shaft to rotate so as to reciprocate in each of a first rotation direction and a second rotation direction opposite to the first rotation direction within the predetermined angular range of the movable portion, to thereby pull the wire, and configured to cause the drive shaft to drive such that the drive shaft is at a specific rotation angle in a range between a first rotation angle and a second rotation angle, to thereby adjust a position at which a slack of the wire is produced, based on the first rotation angle which is the rotation angle detected by the rotation angle detection unit in a case where the slack detection unit detects that the wire is not slack in one of two directions including the first rotation direction and the second rotation direction and the second rotation angle which is the rotation angle detected by the rotation angle detection unit in a case where the slack detection unit detects that the wire is not slack in the other of the two directions;
 a characteristics storage unit configured to store characteristics of respective rotation angles by which the drive shaft is rotated in the first rotation direction and the second rotation direction so as to cover the predetermined angular range of the movable portion and characteristics of an angle of the movable portion to change in accordance with the respective rotation angles associating the characteristics as characteristics of a reference rotation angle representing the respective rotation angles and a reference angle representing the angle corresponding to the reference rotation angle, in advance with each other;
 an angle detection unit configured to detect an angle by which the movable portion actually rotated;
 a storage unit configured to store the rotation angle detected by the rotation angle detection unit and the angle detected by the angle detection unit by associating with each other the rotation angle and the angle in time sequence as passage of time, the storage unit including the characteristics storage unit; and
 a correction unit configured to, when the rotation angle detected by the rotation angle detection unit and the angle detected by the angle detection unit are stored in the storage unit by being associated with each other in time sequence and if the slack detection unit detects that the slack exists, rotate the drive shaft until the stack does not exist, and to correct, in time sequence, the rotation angle detected by the rotation angle detection unit in a state where the slack does not exist and the angle detected by the angle detection unit corresponding to the rotation angle so as to replace a previous reference rotation angle and a previous reference angle stored in the characteristics storage unit with a current reference rotation angle and a current reference angle corresponding to the current reference rotation angle as information associating the current reference rotation angle and the current reference angle.

2. The medical system according to claim 1, wherein the specific rotation angle is equal to the first rotation angle or the second rotation angle.

3. The medical system according to claim 1, wherein the specific rotation angle is a rotation angle intermediate between the first rotation angle and the second rotation angle.

4. The medical system according to claim 1, wherein the slack detection unit detects the slack of the wire by detecting a load applied to the actuator or a load applied to the wire when the movable portion is driven to bend to change the angle of the movable portion.

5. The medical system according to claim 1, wherein the slack detection unit detects the slack of the wire by detecting a load applied to the actuator by detecting an amount of driving force of the actuator or detecting a value of current, or detecting a load applied to the wire by detecting tension acting on the wire, when the movable portion is driven to bend to change the angle of the movable portion.

6. The medical system according to claim 1, wherein the actuator includes a motor configured to pull the wire by rotating.

7. The medical system according to claim 6, wherein the slack adjustment unit causes the drive shaft to drive such that the drive shaft of the motor has the specific rotation angle, to thereby adjust a position at which the slack is produced, based on detection results detected by the slack detection unit at two rotation angles with the slack of the wire removed in the first rotation direction and the second rotation direction as the two mutually opposite directions when the movable portion is rotated by the motor in the first rotation direction and the second rotation direction.

8. The medical system according to claim 7, wherein the slack adjustment unit calculates the specific rotation angle from average values of the two rotation angles over a plurality of times detected respectively when the movable portion is rotated in the first rotation direction and the second rotation direction, reciprocating the plurality of times and causes the drive shaft to drive such that the drive shaft has the specific rotation angle, to thereby adjust a position at which the slack is produced.

9. The medical system according to claim 6, wherein the storage unit stores in advance information about torque of the motor, a rotation angle detected by the rotation angle detection unit, and an angle of the movable portion detected by the angle detection unit in time sequence together with information about time under a driving condition in which the movable portion is driven by the motor.

10. The medical system according to claim 9, wherein even when a command to adjust the slack is not inputted from the slack adjustment command input unit, the slack adjustment unit adjusts the slack of the wire based on the detection result produced by the slack detection unit and updates the information in the storage unit based on a slack adjustment result.

11. The medical system according to claim 6, wherein
a characteristics storage unit stores in advance characteristics of a rotation angle of the drive shaft of the motor and the angle of the movable portion corresponding to a rotation angle as characteristics of the reference rotation angle and the reference angle corresponding to the reference rotation angle; and
a correction unit corrects and replaces the previous reference rotation angle stored in the characteristics storage unit with the previous reference angle corresponding to the previous reference rotation angle with a current rotation angle of the drive shaft of the motor and a current angle of the movable portion corresponding to the current rotation angle stored in the storage unit stored in the characteristics storage unit, based on a slack adjustment result of the wire produced by the slack adjustment unit.

12. The medical system according to claim 1, wherein the medical instrument includes an endoscope equipped with an insertion portion which is inserted into a subject and is provided with a bending portion in which a bending angle of the movable portion is changed as the angle.

13. The medical system according to claim 12, wherein the endoscope comprises an image pickup device; the medical system further comprises a signal processing apparatus configured to perform signal processing for the image pickup device; and the slack adjustment command is inputted from the slack adjustment command input unit in conjunction with a command input for the signal processing apparatus to perform signal processing.

14. The medical system according to claim 12, wherein when a command to adjust the slack is inputted, the slack adjustment unit adjusts the slack so as to achieve a predetermined state of adjustment in which the wire is not slack in one of the two directions or the wire has a same amount of slack in the two directions based on a detection result detected by the slack detection unit regarding the slack of the wire in the two directions when the bending angle of the bending portion is changed so as to reciprocate the bending portion in the two directions.

15. The medical system according to claim 12, wherein the endoscope comprises an image pickup device; the medical system further comprises a signal processing apparatus configured to perform signal processing for the image pickup device and generate a video signal of an endoscopic image to be displayed on a display device; and the signal processing apparatus superimposes a slack adjustment result produced by the slack adjustment unit on the video signal and displays the slack adjustment result together with the endoscopic image on the display device.

16. The medical system according to claim 1, wherein the medical instrument includes a treatment instrument used to administer therapeutic treatment to a subject and provided with a bending portion in which a bending angle of the movable portion is changed as the angle.

17. The medical system according to claim 1, wherein the slack adjustment command input unit includes a switch.

18. The medical system according to claim 1, wherein if a setting of an initial angle of the movable portion is set at an approximate center of a range from the first rotation angle to the second rotation angle in an initial state in which the movable portion is freed from being driven by the actuator, the slack adjustment unit adjusts the slack of the wire so as to give equal amounts of slack to the wire in the two directions on both sides of the initial angle.

19. The medical system according to claim 1, wherein the slack adjustment unit makes an adjustment to eliminate an amount of slack of the wire in one of the two directions on both sides of an initial angle of the movable portion in an initial state in which the movable portion is freed from being driven by the actuator.

20. The medical system according to claim 1, further comprising a storage control unit configured to control the storage unit to store the rotation angle detected by the rotation angle detection unit and the angle detected by the angle detection unit in time sequence for each certain time period.

21. The medical system according to claim 1, wherein the storage unit stores, in addition to the rotation angle detected by the rotation angle detection unit and the angle detected by the angle detection unit, an amount of driving force with which the actuator rotates and drives the drive shaft, in time sequence as the passage of time.

22. The medical system according to claim 1, wherein the correction unit includes a history characteristics correcting unit configured to, when correcting the information associating with each other the previous reference angle and the previous reference angle stored in the characteristics unit, use a shifted value of the previous reference rotation angle by the rotation angle by which the drive shaft was rotated until the slack no longer exists, and the reference angle corresponding to the shifted reference rotation angle, to thereby correct the information.

23. The medical system according to claim 1, wherein the control unit controls driving of the actuator by referring to the information which associates the reference rotation angle and the reference angle with each other and is stored in the characteristics storage unit.

* * * * *